(12) United States Patent
Skierczynski et al.

(10) Patent No.: US 6,934,636 B1
(45) Date of Patent: Aug. 23, 2005

(54) METHODS OF GENETIC CLUSTER ANALYSIS AND USES THEREOF

(75) Inventors: Boguslaw A. Skierczynski, Oceanside, CA (US); Nicholas J. Schork, San Diego, CA (US)

(73) Assignee: Genset, S.A. (FR)

( * ) Notice: Subject to any disclaimer, the term of this patent is extended or adjusted under 35 U.S.C. 154(b) by 995 days.

(21) Appl. No.: 09/693,333

(22) Filed: Oct. 20, 2000

Related U.S. Application Data

(60) Provisional application No. 60/161,231, filed on Oct. 22, 1999, and provisional application No. 60/216,897, filed on Jul. 7, 2000.

(51) Int. Cl.[7] .......................... G06F 19/00; G11C 17/00; G05B 15/00
(52) U.S. Cl. ................................ 702/19; 365/94; 700/1
(58) Field of Search ............................ 702/19; 365/94; 700/1

(56) References Cited

U.S. PATENT DOCUMENTS

2002/0052692 A1 * 5/2002 Fahy ........................... 702/19

FOREIGN PATENT DOCUMENTS

| WO | WO 99 09218 A1 | 2/1999 |
| WO | WO 01/20536 A2 | 3/2001 |

OTHER PUBLICATIONS

Ralf–Herwig, et al.; "Large–Scale Clustering of cDNA–Fingerprinting Data", Genome Research, Cold Spring Harbor Laboratory Press; vol. 9, Nov. 1999; pp. 1093–1105; XP002176537; ISSN: 1088–9051.

Chen, Y., et al.; "Clustering Analysis for Gene Expression Data"; Proceedings of the National Academy of Sciences of USA, National Academy of Science, Washington, D.C.; vol. 95, Jan. 1999, pp. 14863–14964; XP001001103.

Alon, U., et al.; "Broad patterns of gene expression revealed by clustering analysis of tumor and normal colon tissues probed by oligonucleotide arrays"; Proceedings of the National Academy of Sciences of USA, National Academy of Science, Washington, D.C.; vol. 96, 1999; pp. 6745–6750; XP000900484.

Eisen, M., et al.; "Cluster analysis and display of genome–wide expression patterns"; Proceedings of the National Academy of Sciences of USA, National Academy of Science, Washington, D.C.; vol. 95, Dec. 1998; pp. 14863–14868; XO002140966; ISSN: 0027–8424.

Pritchard, et al.; "Use of Unlimited Genetic Markes to Detect Population Stratification In Association Studies"; Am. J. Hum. Genet., vol. 65, pp. 220–228, 1999; The American Society of Human Genetics.

Lamboy, Warren: "Computing Genetic Similarity Coefficients from RAPD Data: The Effects of PCR Artifacts"; PCR Methods and Applications, pp. 31–37; Cold Spring Harbor Laboratory Press.

Mountain, et al: "Multilocus Genotypes, a Tree of Individuals, and Human Evolutionary History"; Am. J. Hum. Genet., vol. 61, pp. 705–718, 1997; The American Society of Human Genetics.

Jasienski, M., et al.; "Phenotypic Plasticity and Similarity of DNA among Genotypes of an Annual Plant"; Heredity. vol. 78, pp. 176–181; 1997; The Genetical Society of Great Britain.

Curnow, R.N.; "Estimating Genetic Similarities within and between Populations"; Journal of Agricultural, Biological and Environmental Statistics, vol. 3, No. 4, pp. 347–358; American Statistical Association and the International Biometric Society, (1998).

Bowcock, A.M., et al: "High Resolution of Human Evolutionary Trees with Polymorphic Microsatellites"; Nature, vol. 358, Mar. 31, 1994, pp. 455–457.

Ciampolini, R., et al.: "Individual Multilocus Genotypes Using Microsatellie Polymorphisms to Permit the Analysis of the Genetic Variability Within and Between Italian Beef Cattle Breeds"; J. Anim. Sci., vol. 73, pp. 3259–3268, (1995).

* cited by examiner

Primary Examiner—John S. Brusca
(74) Attorney, Agent, or Firm—Saliwanchik, Lloyd & Saliwanchik

(57) ABSTRACT

The present invention is primarily directed to methods of genetic cluster analysis for use in determining the homogeneity and/or heterogeneity of a population or sub-population. Determination of the heterogeneity or homogeneity of a population sample is important in many areas including DNA fingerprinting in forensics and population-based studies such as clinical trials, case-control studies of risk factors, and gene mapping studies.

16 Claims, 22 Drawing Sheets

SEQUENCE LISTING

<160> NUMBER OF SEQ ID NOS: 189

<210> SEQ ID NO 1
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 10-102-294 : polymorphic base C or T

```
<400> SEQUENCE: 1
gcgcggctgc gcttctccat caaytgaaga agacaccacc attctga          47

<210> SEQ ID NO 2
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 10-24-234 : polymorphic base A or G

<400> SEQUENCE: 2
caggagcgct gtcggcagga ggtrcaagag cttctgaagg accgtga          47

<210> SEQ ID NO 3
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 10-88-81 : polymorphic base C or T

<400> SEQUENCE: 3
atattaaaag tataactgga aaayctatgt tgaaatcaac caaacat          47

<210> SEQ ID NO 4
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 4-14-35 : polymorphic base C or T

<400> SEQUENCE: 4
atccaacaca gaaaccgcta aaaycaggca gaagctgtct gcagaga          47

<210> SEQ ID NO 5
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 4-20-149 : polymorphic base C or T

<400> SEQUENCE: 5
tttttgctgt gtcttcaaag tgaytcttgg tttattgcct gctaagg          47

<210> SEQ ID NO 6
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 4-22-174 : polymorphic base A or C

<400> SEQUENCE: 6
ggattgtgca gaagttgcct ttcmtgttca aaaatgttaa tttgttt          47

<210> SEQ ID NO 7
<211> LENGTH: 47
<212> TYPE: DNA
<213> ORGANISM: Homo Sapiens
```

```
<220> FEATURE:
<221> NAME/KEY: allele
<222> LOCATION: 24
<223> OTHER INFORMATION: 4-26-29 : polymorphic base A or G
<220> FEATURE:
<221> NAME/KEY: misc_feature
<222> LOCATION: 7
<223> OTHER INFORMATION: n=a, g, c or t

<400> SEQUENCE: 7
ccctgtnaga cacgtcctgt atcrttgttg agatgggaaa gtgcatc      47

<210> SEQ ID NO 8
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 4-3-130 : polymorphic base A or G

<400> SEQUENCE: 8
tattgggcct aaaacagtat tctrtaaagc ttaaattggt attaact       47

<210> SEQ ID NO 9
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 4-32-120 : polymorphic base G or C

<400> SEQUENCE: 9
gaaactaaaa gacaatattc agtstgagat tttccaagtt ctttatg       47

<210> SEQ ID NO 10
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 4-38-83 : polymorphic base G or T

<400> SEQUENCE: 10
ggcvgaggct aaactttttt tttktttggc aatgctgttg agaatat       47

<210> SEQ ID NO 11
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 4-4-187 : polymorphic base A or T

<400> SEQUENCE: 11
tataaacaga aacatggatg agtwaaaaaa aaaaaaaaa aaaaaaa       47

<210> SEQ ID NO 12
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 4-42-401 : polymorphic base A or C
```

-continued

```
<400> SEQUENCE: 12
taagaaagaa ttctgtgttc tggmcaaagt ttaaacccac agagmca                47

<210> SEQ ID NO 13
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 4-43-70 : polymorphic base G or C

<400> SEQUENCE: 13
atcgcctcca ttattctcaa aaasaccatg ggacacaaca caagaag                47

<210> SEQ ID NO 14
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 4-50-209 : polymorphic base C or T

<400> SEQUENCE: 14
atatagagtg tgcatccctg acaytgaaac tgaaggcttt atggttt                47

<210> SEQ ID NO 15
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 4-52-88 : polymorphic base C or T

<400> SEQUENCE: 15
tccatgtcat tattattcaa aagyttaaaa aatacacaag gtgaaaa                47

<210> SEQ ID NO 16
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 4-53-258 : polymorphic base A or G

<400> SEQUENCE: 16
gagaaatcat gcagagagaa tgcrttctca ctcaaatttt aacctaa                47

<210> SEQ ID NO 17
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 4-54-283 : polymorphic base A or T

<400> SEQUENCE: 17
aagtagtttt tcacactttc tctwtgatac aatcgatggc ttaatct                47

<210> SEQ ID NO 18
<211> LENGTH: 47
<212> TYPE: DNA
<213> ORGANISM: Homo Sapiens
```

```
<220> FEATURE:
<221> NAME/KEY: allele
<222> LOCATION: 24
<223> OTHER INFORMATION: 4-55-70 : polymorphic base A or T

<400> SEQUENCE: 18
tattaagaac ctaggtttta aaawactctc tatcgtatac atcttta                47

<210> SEQ ID NO 19
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 4-56-159 : polymorphic base C or T

<400> SEQUENCE: 19
aagttttcct tctcttctgt agaygtctcc atgttacagt caactat                47

<210> SEQ ID NO 20
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 4-58-289 : polymorphic base G or C

<400> SEQUENCE: 20
catacctgca gcctgctttt ggtsaggggt gactacttta cctgcaa                47

<210> SEQ ID NO 21
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 4-60-293 : polymorphic base C or T

<400> SEQUENCE: 21
aagtttcagt atttcttagc agaygaagcc agcaggaagt cctccta                47

<210> SEQ ID NO 22
<211> LENGTH: 48
<212> TYPE: DNA
<213> ORGANISM: Homo Sapiens
<220> FEATURE:
<221> NAME/KEY: allele
<222> LOCATION: 24
<223> OTHER INFORMATION: 4-76-222 : deletion gt

<400> SEQUENCE: 22
aacatccttc tggaaaacac tgtgtaagct ttcagtgcga ataaacat               48

<210> SEQ ID NO 23
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 4-77-151 : polymorphic base G or C

<400> SEQUENCE: 23
gctgttcaga ctaaacttgg agastacagt cagtcagaga acttgct                47
```

<210> SEQ ID NO 24
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 4-84-241 : polymorphic base G or T

<400> SEQUENCE: 24
gaaaaaaaaa tagtgactgc cackgtgaat aattcagttc ttcagaa         47

<210> SEQ ID NO 25
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 4-86-206 : polymorphic base A or G

<400> SEQUENCE: 25
gtattcaaat caggacacac cacraatggc atctacacgt taacatt         47

<210> SEQ ID NO 26
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 4-88-349 : polymorphic base G or C

<400> SEQUENCE: 26
gaaactaaaa gacaatattc agtstgagat tttccaagtt ctttatg         47

<210> SEQ ID NO 27
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 4-89-87 : polymorphic base C or T

<400> SEQUENCE: 27
ttcttccctg aacgctggtt tcayatagtt tttgtgttga gaataga         47

<210> SEQ ID NO 28
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 4-9-226 : polymorphic base A or G

<400> SEQUENCE: 28
ctgacaaagg aaagtggatg tttrgagggg acgagggaag catcagt         47

<210> SEQ ID NO 29
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 5-11-158 : polymorphic base A or G

```
<400> SEQUENCE: 29 gattttttt ggtaaaactg tgargagcta ggatatatac ttggtga                47

<210> SEQ ID NO 30
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 5-14-165 : polymorphic base C or T

<400> SEQUENCE: 30
ttaaaagtac tcagtgtaga aatygctagc ccttaattct tttccag                47

<210> SEQ ID NO 31
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 5-15-219 : polymorphic base A or T

<400> SEQUENCE: 31
atattagctt caaaggcttt taawctcaat gcgaacattc tacggga                47

<210> SEQ ID NO 32
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 5-2-213 : polymorphic base C or T

<400> SEQUENCE: 32
atcctggaac tttgattgtg ataygtgggc atgttcctag tgacgca                47

<210> SEQ ID NO 33
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 5-3-248 : polymorphic base A or G

<400> SEQUENCE: 33
tttgagatcg tgattatggt gctraaggac aaattccagg taggttt                47

<210> SEQ ID NO 34
<211> LENGTH: 45
<212> TYPE: DNA
<213> ORGANISM: Homo Sapiens
<220> FEATURE:
<221> NAME/KEY: allele
<222> LOCATION: 22
<223> OTHER INFORMATION: 5-5-21 : polymorphic base A or G

<400> SEQUENCE: 34
aaaggacccc agtgtdcaag trtatttttg gatcatagtt ttcaa                  45

<210> SEQ ID NO 35
<211> LENGTH: 47
<212> TYPE: DNA
<213> ORGANISM: Homo Sapiens
```

```
<220> FEATURE:
<221> NAME/KEY: allele
<222> LOCATION: 24
<223> OTHER INFORMATION: 5-7-195 : polymorphic base G or C

<400> SEQUENCE: 35
ctgactgtgg cttcttttca gagsctgcca ttcgctgcaa ggttgaa                47

<210> SEQ ID NO 36
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 99-1051-284 : polymorphic base A or G

<400> SEQUENCE: 36
aatctcccgg ttttaatgtt tcaraacatt gctcaggcca tacaaaa                47

<210> SEQ ID NO 37
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 99-1182-310 : polymorphic base A or G

<400> SEQUENCE: 37
aacagcaccc ttcctttcct ttgrataact gtgcctactg catttcc                47

<210> SEQ ID NO 38
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 99-123-381 : polymorphic base C or T

<400> SEQUENCE: 38
tttctcatcc tcacacctca ctgygcccct cctgaaccca ctcctttt               47

<210> SEQ ID NO 39
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 99-128-60 : polymorphic base C or T

<400> SEQUENCE: 39
gcactgtgac ccaggcgcta ggtycctctt acagtgacac tccgaca                47

<210> SEQ ID NO 40
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 99-1453-204 : polymorphic base C or T

<400> SEQUENCE: 40
atcaggcccc aaaaggcact gaayraaaca gcagtcacat cactccc                47
```

```
<210> SEQ ID NO 41
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 99-1480-290 : polymorphic base G or T

<400> SEQUENCE: 41
tgcaccatct tcaccacaac ccckggcaac cactgatcct tttactg          47

<210> SEQ ID NO 42
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 99-1490-381 : polymorphic base C or T

<400> SEQUENCE: 42
tgcacagtgg aaataccatg tcayggtacg ctactgtgca tctcttc          47

<210> SEQ ID NO 43
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 99-1493-280 : polymorphic base A or G

<400> SEQUENCE: 43
ggatgacaga gtattgttgg aggratgggg tttggctgct tgttttt          47

<210> SEQ ID NO 44
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 99-1572-440 : polymorphic base C or T

<400> SEQUENCE: 44
agcccaggag tttgagacca gccygggcaa cacagtggac cctgtct          47

<210> SEQ ID NO 45
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 99-1582-430 : polymorphic base C or T

<400> SEQUENCE: 45
gtgaactgta acctaactgg atgygtaaac agactataac ctactct          47

<210> SEQ ID NO 46
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 99-1585-373 : polymorphic base C or T
```

```
<400> SEQUENCE: 46
gtcagcaacg aacatgtgag caayagaatc tacgtcataa tkaagtt              47

<210> SEQ ID NO 47
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 99-1591-235 : polymorphic base A or G

<400> SEQUENCE: 47
gtccgaggtg attttctccc actrctctcc taggtggtgc catccaa              47

<210> SEQ ID NO 48
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 99-1602-200 : polymorphic base G or C

<400> SEQUENCE: 48
aatcgagacc atcctggcta acasagtgaa accccgtctc tactaaa              47

<210> SEQ ID NO 49
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 99-1605-112 : polymorphic base A or G

<400> SEQUENCE: 49
tgatgaaagc taattgggcc tcaragtatc aaatggtctc tcccgcc              47

<210> SEQ ID NO 50
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 99-1607-373 : polymorphic base A or G

<400> SEQUENCE: 50
gagtaaagga cgtgccatcc ccaratatgc cagatggggg gtattga              47

<210> SEQ ID NO 51
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 99-2222-459 : polymorphic base C or T

<400> SEQUENCE: 51
gctggcaacc tcccctacct catyttctgt ctttgttccc ctcactc              47

<210> SEQ ID NO 52
<211> LENGTH: 47
<212> TYPE: DNA
<213> ORGANISM: Homo Sapiens
```

```
<220> FEATURE:
<221> NAME/KEY: allele
<222> LOCATION: 24
<223> OTHER INFORMATION: 99-2797-399 : polymorphic base C or T

<400> SEQUENCE: 52
ttataaagga agaaaaaggt agcygacttc gtttgttctg cttaatg                47

<210> SEQ ID NO 53
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 99-2914-48 : polymorphic base A or G

<400> SEQUENCE: 53
atctgtagat cactttgggt agtrtggaca ttttatcaat tttaatt                47

<210> SEQ ID NO 54
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 99-3047-395 : polymorphic base A or G

<400> SEQUENCE: 54
gatctatagg agaatccatg gtgragccct atcttttgtc atatgag                47

<210> SEQ ID NO 55
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 99-3484-96 : polymorphic base A or G

<400> SEQUENCE: 55
aaagtttaac tattaaagaa agarttcctg ggatgccacc taaaacc                47

<210> SEQ ID NO 56
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 99-4182-113 : polymorphic base A or G

<400> SEQUENCE: 56
gttatttgta aatattggtt ttgrtgctaa cctagaattc catcaaa                47

<210> SEQ ID NO 57
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 99-4202-223 : polymorphic base C or T

<400> SEQUENCE: 57
attttcagct tatgagtctc tgcyctggta agttgtgatt gtctgtc                47
```

<210> SEQ ID NO 58
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 99-5339-196 : polymorphic base A or G

<400> SEQUENCE: 58
caaatatatc cagaagtcac tttrcatttt taatcaataa gtgagta          47

<210> SEQ ID NO 59
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 99-5575-330 : polymorphic base C or T

<400> SEQUENCE: 59
tgagggagag actgaattct ttcytgaaac agaaatattc ctatctc          47

<210> SEQ ID NO 60
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 99-619-141 : polymorphic base C or T

<400> SEQUENCE: 60
tacattgtct atcaaacatt gtayccttg gtacccagga cagcacc           47

<210> SEQ ID NO 61
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 99-622-95 : polymorphic base A or G

<400> SEQUENCE: 61
accacttatt ttttaaacct agarttgaaa ggtgtaaaaa tgtcatt          47

<210> SEQ ID NO 62
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 99-7183-338 : polymorphic base A or G

<400> SEQUENCE: 62 tttttttaaat tactgttgtg tccrtactgt tagcactggg agatttc         47

<210> SEQ ID NO 63
<211> LENGTH: 47
<212> TYPE: DNA
<213> ORGANISM: Homo Sapiens
<220> FEATURE:
<221> NAME/KEY: allele
<222> LOCATION: 24
<223> OTHER INFORMATION: 99-952-252 : polymorphic base G or C

```
<400> SEQUENCE: 63
ctcaccatac cgaattactg tgtstgtgaa tcttgtcaac aatccat                    47

<210> SEQ ID NO 64
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: upstream amplification primer 10-102 for SEQ 1,

<400> SEQUENCE: 64
agagagctgt gggaggac                                                    18

<210> SEQ ID NO 65
<211> LENGTH: 20
<212> TYPE: DNA
<213> ORGANISM: Homo Sapiens
<220> FEATURE:
<221> NAME/KEY: primer_bind
<222> LOCATION: 1..20
<223> OTHER INFORMATION: upstream amplification primer 10-24 for SEQ 2,

<400> SEQUENCE: 65
tccattccag gaacagggtg                                                  20

<210> SEQ ID NO 66
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: upstream amplification primer 10-88 for SEQ 3,

<400> SEQUENCE: 66
taaatgaccg tgctacag                                                    18

<210> SEQ ID NO 67
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: upstream amplification primer 4-14 for SEQ 4,

<400> SEQUENCE: 67
tctaacctct catccaac                                                    18

<210> SEQ ID NO 68
<211> LENGTH: 19
<212> TYPE: DNA
<213> ORGANISM: Homo Sapiens
<220> FEATURE:
<221> NAME/KEY: primer_bind
<222> LOCATION: 1..19
<223> OTHER INFORMATION: upstream amplification primer 4-20 for SEQ 5,

<400> SEQUENCE: 68
gttatcgtga gactttttc                                                   19

<210> SEQ ID NO 69
<211> LENGTH: 18
<212> TYPE: DNA
<213> ORGANISM: Homo Sapiens
```

```
<220> FEATURE:
<221> NAME/KEY: primer_bind
<222> LOCATION: 1..18
<223> OTHER INFORMATION: upstream amplification primer 4-22 for SEQ 6,

<400> SEQUENCE: 69
tgctggtgct gtgataac                                                 18

<210> SEQ ID NO 70
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: upstream amplification primer 4-26 for SEQ 7,

<400> SEQUENCE: 70
tacagccctg taagacac                                                 18

<210> SEQ ID NO 71
<211> LENGTH: 19
<212> TYPE: DNA
<213> ORGANISM: Homo Sapiens
<220> FEATURE:
<221> NAME/KEY: primer_bind
<222> LOCATION: 1..19
<223> OTHER INFORMATION: upstream amplification primer 4-3 for SEQ 8,

<400> SEQUENCE: 71
cagtatgttc aatgcacag                                                19

<210> SEQ ID NO 72
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: upstream amplification primer 4-32 for SEQ 9,

<400> SEQUENCE: 72
tttcttccct gaacgctg                                                 18

<210> SEQ ID NO 73
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: upstream amplification primer 4-38 for SEQ 10,

<400> SEQUENCE: 73
aaaacatcga catgggac                                                 18

<210> SEQ ID NO 74
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: upstream amplification primer 4-4 for SEQ 11,
```

```
<400> SEQUENCE: 74
agcatttcga gtcatgtg                                              18

<210> SEQ ID NO 75
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: upstream amplification primer 4-42 for SEQ 12,

<400> SEQUENCE: 75
ccctctttcc tcatgtag                                              18

<210> SEQ ID NO 76
<211> LENGTH: 19
<212> TYPE: DNA
<213> ORGANISM: Homo Sapiens
<220> FEATURE:
<221> NAME/KEY: primer_bind
<222> LOCATION: 1..19
<223> OTHER INFORMATION: upstream amplification primer 4-43 for SEQ 13,

<400> SEQUENCE: 76
taactcgtaa acagagaac                                             19

<210> SEQ ID NO 77
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: upstream amplification primer 4-50 for SEQ 14,

<400> SEQUENCE: 77
gcgtattgaa gctcttg                                               18

<210> SEQ ID NO 78
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: upstream amplification primer 4-52 for SEQ 15,

<400> SEQUENCE: 78
aacacgggga ttttaggc                                              18

<210> SEQ ID NO 79
<211> LENGTH: 19
<212> TYPE: DNA
<213> ORGANISM: Homo Sapiens
<220> FEATURE:
<221> NAME/KEY: primer_bind
<222> LOCATION: 1..19
<223> OTHER INFORMATION: upstream amplification primer 4-53 for SEQ 16,

<400> SEQUENCE: 79
cacatactaa ggctaatgg                                             19

<210> SEQ ID NO 80
<211> LENGTH: 18
<212> TYPE: DNA
<213> ORGANISM: Homo Sapiens
```

```
<220> FEATURE:
<221> NAME/KEY: primer_bind
<222> LOCATION: 1..18
<223> OTHER INFORMATION: upstream amplification primer 4-54 for SEQ 17,

<400> SEQUENCE: 80
gttgctggaa cctatttg                                                18

<210> SEQ ID NO 81
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: upstream amplification primer 4-55 for SEQ 18,

<400> SEQUENCE: 81
tcgatggctt aatctacc                                                18

<210> SEQ ID NO 82
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: upstream amplification primer 4-56 for SEQ 19,

<400> SEQUENCE: 82
aaagaggagt aaatgggg                                                18

<210> SEQ ID NO 83
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: upstream amplification primer 4-58 for SEQ 20,

<400> SEQUENCE: 83
tccccacagc taagagcc                                                18

<210> SEQ ID NO 84
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: upstream amplification primer 4-60 for SEQ 21,

<400> SEQUENCE: 84
atacctaatt tcaggggg                                                18

<210> SEQ ID NO 85
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: upstream amplification primer 4-76 for SEQ 22,

<400> SEQUENCE: 85
gtagagcaga catgccgc                                                18
```

```
<210> SEQ ID NO 86
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: upstream amplification primer 4-77 for SEQ 23,

<400> SEQUENCE: 86
tgttgattta caggcggc                                                  18

<210> SEQ ID NO 87
<211> LENGTH: 19
<212> TYPE: DNA
<213> ORGANISM: Homo Sapiens
<220> FEATURE:
<221> NAME/KEY: primer_bind
<222> LOCATION: 1..19
<223> OTHER INFORMATION: upstream amplification primer 4-84 for SEQ 24,

<400> SEQUENCE: 87
ttaacagagt accttggag                                                 19

<210> SEQ ID NO 88
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: upstream amplification primer 4-86 for SEQ 25,

<400> SEQUENCE: 88
gtacagcctt ttgcttac                                                  18

<210> SEQ ID NO 89
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: upstream amplification primer 4-88 for SEQ 26,

<400> SEQUENCE: 89
aacgtgtcat agaaagcc                                                  18

<210> SEQ ID NO 90
<211> LENGTH: 19
<212> TYPE: DNA
<213> ORGANISM: Homo Sapiens
<220> FEATURE:
<221> NAME/KEY: primer_bind
<222> LOCATION: 1..19
<223> OTHER INFORMATION: upstream amplification primer 4-89 for SEQ 27,

<400> SEQUENCE: 90
gctgatgagt tagataacc                                                 19

<210> SEQ ID NO 91
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: upstream amplification primer 4-9 for SEQ 28,
```

```
<400> SEQUENCE: 91
tgcaccttga gcagtttg                                                18

<210> SEQ ID NO 92
<211> LENGTH: 19
<212> TYPE: DNA
<213> ORGANISM: Homo Sapiens
<220> FEATURE:
<221> NAME/KEY: primer_bind
<222> LOCATION: 1..19
<223> OTHER INFORMATION: upstream amplification primer 5-11 for SEQ 29,

<400> SEQUENCE: 92
ggggcagcaa cacttatag                                               19

<210> SEQ ID NO 93
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: upstream amplification primer 5-14 for SEQ 30,

<400> SEQUENCE: 93
aaagctcagt cagtgagg                                                18

<210> SEQ ID NO 94
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: upstream amplification primer 5-15 for SEQ 31,

<400> SEQUENCE: 94
cactcacatc attccttg                                                18

<210> SEQ ID NO 95
<211> LENGTH: 20
<212> TYPE: DNA
<213> ORGANISM: Homo Sapiens
<220> FEATURE:
<221> NAME/KEY: primer_bind
<222> LOCATION: 1..20
<223> OTHER INFORMATION: upstream amplification primer 5-2 for SEQ 32,

<400> SEQUENCE: 95
gaaagatgac ttggaaaatg                                              20

<210> SEQ ID NO 96
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: upstream amplification primer 5-3 for SEQ 33,

<400> SEQUENCE: 96
gtggctttcc tttctgag                                                18

<210> SEQ ID NO 97
<211> LENGTH: 19
<212> TYPE: DNA
<213> ORGANISM: Homo Sapiens
```

```
<220> FEATURE:
<221> NAME/KEY: primer_bind
<222> LOCATION: 1..19
<223> OTHER INFORMATION: upstream amplification primer 5-5 for SEQ 34,

<400> SEQUENCE: 97
aaaggacccc agtgtcaag                                                    19

<210> SEQ ID NO 98
<211> LENGTH: 19
<212> TYPE: DNA
<213> ORGANISM: Homo Sapiens
<220> FEATURE:
<221> NAME/KEY: primer_bind
<222> LOCATION: 1..19
<223> OTHER INFORMATION: upstream amplification primer 5-7 for SEQ 35,

<400> SEQUENCE: 98
tgagtgtttg cttcgagcc                                                    19

<210> SEQ ID NO 99
<211> LENGTH: 20
<212> TYPE: DNA
<213> ORGANISM: Homo Sapiens
<220> FEATURE:
<221> NAME/KEY: primer_bind
<222> LOCATION: 1..20
<223> OTHER INFORMATION: upstream amplification primer 99-1051 for SEQ
      36,

<400> SEQUENCE: 99
cttgtgatgt gaagtagatg                                                   20

<210> SEQ ID NO 100
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: upstream amplification primer 99-1182 for SEQ
      37,

<400> SEQUENCE: 100
gcattaactg aacccatc                                                     18

<210> SEQ ID NO 101
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: upstream amplification primer 99-123 for SEQ
      38,

<400> SEQUENCE: 101
aaagccagga ctagaagg                                                     18

<210> SEQ ID NO 102
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: upstream amplification primer 99-128 for SEQ
      39,
```

```
<400> SEQUENCE: 102
gaccagggtt taagttag                                              18

<210> SEQ ID NO 103
<211> LENGTH: 20
<212> TYPE: DNA
<213> ORGANISM: Homo Sapiens
<220> FEATURE:
<221> NAME/KEY: primer_bind
<222> LOCATION: 1..20
<223> OTHER INFORMATION: upstream amplification primer 99-1453 for SEQ
      40,

<400> SEQUENCE: 103
gtaggtatat ggaaagtgtg                                            20

<210> SEQ ID NO 104
<211> LENGTH: 19
<212> TYPE: DNA
<213> ORGANISM: Homo Sapiens
<220> FEATURE:
<221> NAME/KEY: primer_bind
<222> LOCATION: 1..19
<223> OTHER INFORMATION: upstream amplification primer 99-1480 for SEQ
      41,

<400> SEQUENCE: 104
ttgcacaaaa ggtatagag                                             19

<210> SEQ ID NO 105
<211> LENGTH: 19
<212> TYPE: DNA
<213> ORGANISM: Homo Sapiens
<220> FEATURE:
<221> NAME/KEY: primer_bind
<222> LOCATION: 1..19
<223> OTHER INFORMATION: upstream amplification primer 99-1490 for SEQ
      42,

<400> SEQUENCE: 105
aaggcaacag cgttgtgac                                             19

<210> SEQ ID NO 106
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: upstream amplification primer 99-1493 for SEQ
      43,

<400> SEQUENCE: 106
tttttggggt tttcagtg                                              18

<210> SEQ ID NO 107
<211> LENGTH: 19
<212> TYPE: DNA
<213> ORGANISM: Homo Sapiens
<220> FEATURE:
<221> NAME/KEY: primer_bind
<222> LOCATION: 1..19
<223> OTHER INFORMATION: upstream amplification primer 99-1572 for SEQ
      44,
```

-continued

```
<400> SEQUENCE: 107
ataatgtaag agatgtggg                                              19

<210> SEQ ID NO 108
<211> LENGTH: 19
<212> TYPE: DNA
<213> ORGANISM: Homo Sapiens
<220> FEATURE:
<221> NAME/KEY: primer_bind
<222> LOCATION: 1..19
<223> OTHER INFORMATION: upstream amplification primer 99-1582 for SEQ
      45,

<400> SEQUENCE: 108
cagcactact gataaattg                                              19

<210> SEQ ID NO 109
<211> LENGTH: 20
<212> TYPE: DNA
<213> ORGANISM: Homo Sapiens
<220> FEATURE:
<221> NAME/KEY: primer_bind
<222> LOCATION: 1..20
<223> OTHER INFORMATION: upstream amplification primer 99-1585 for SEQ
      46,

<400> SEQUENCE: 109
cctgcaacat ttttaatgtg                                             20

<210> SEQ ID NO 110
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: upstream amplification primer 99-1591 for SEQ
      47,

<400> SEQUENCE: 110
tcccatttct caacacac                                               18

<210> SEQ ID NO 111
<211> LENGTH: 19
<212> TYPE: DNA
<213> ORGANISM: Homo Sapiens
<220> FEATURE:
<221> NAME/KEY: primer_bind
<222> LOCATION: 1..19
<223> OTHER INFORMATION: upstream amplification primer 99-1602 for SEQ
      48,

<400> SEQUENCE: 111
atccttccaa acttttctc                                              19

<210> SEQ ID NO 112
<211> LENGTH: 21
<212> TYPE: DNA
<213> ORGANISM: Homo Sapiens
<220> FEATURE:
<221> NAME/KEY: primer_bind
<222> LOCATION: 1..21
<223> OTHER INFORMATION: upstream amplification primer 99-1605 for SEQ
      49,

<400> SEQUENCE: 112
gaaatcagac ttacagcaat g                                           21
```

<210> SEQ ID NO 113
<211> LENGTH: 19
<212> TYPE: DNA
<213> ORGANISM: Homo Sapiens
<220> FEATURE:
<221> NAME/KEY: primer_bind
<222> LOCATION: 1..19
<223> OTHER INFORMATION: upstream amplification primer 99-1607 for SEQ
      50,

<400> SEQUENCE: 113
gttgggaaga gttttgtag                                                  19

<210> SEQ ID NO 114
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: upstream amplification primer 99-2222 for SEQ
      51,

<400> SEQUENCE: 114
ataagcaggc tttctagg                                                   18

<210> SEQ ID NO 115
<211> LENGTH: 20
<212> TYPE: DNA
<213> ORGANISM: Homo Sapiens
<220> FEATURE:
<221> NAME/KEY: primer_bind
<222> LOCATION: 1..20
<223> OTHER INFORMATION: upstream amplification primer 99-2797 for SEQ
      52,

<400> SEQUENCE: 115
ggtattgtgt agatgtcagg                                                 20

<210> SEQ ID NO 116
<211> LENGTH: 19
<212> TYPE: DNA
<213> ORGANISM: Homo Sapiens
<220> FEATURE:
<221> NAME/KEY: primer_bind
<222> LOCATION: 1..19
<223> OTHER INFORMATION: upstream amplification primer 99-2914 for SEQ
      53,

<400> SEQUENCE: 116
ggaattttgg tagagattg                                                  19

<210> SEQ ID NO 117
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: upstream amplification primer 99-3047 for SEQ
      54,

<400> SEQUENCE: 117
ccttccttct tttggctc                                                   18

<210> SEQ ID NO 118
<211> LENGTH: 20
<212> TYPE: DNA
<213> ORGANISM: Homo Sapiens

```
<220> FEATURE:
<221> NAME/KEY: primer_bind
<222> LOCATION: 1..20
<223> OTHER INFORMATION: upstream amplification primer 99-3484 for SEQ
      55,

<400> SEQUENCE: 118 cacccctaagc aataatatcc                                              20

<210> SEQ ID NO 119
<211> LENGTH: 19
<212> TYPE: DNA
<213> ORGANISM: Homo Sapiens
<220> FEATURE:
<221> NAME/KEY: primer_bind
<222> LOCATION: 1..19
<223> OTHER INFORMATION: upstream amplification primer 99-4182 for SEQ
      56,

<400> SEQUENCE: 119
taaaaagcca agagcttac                                                19

<210> SEQ ID NO 120
<211> LENGTH: 19
<212> TYPE: DNA
<213> ORGANISM: Homo Sapiens
<220> FEATURE:
<221> NAME/KEY: primer_bind
<222> LOCATION: 1..19
<223> OTHER INFORMATION: upstream amplification primer 99-4202 for SEQ
      57,

<400> SEQUENCE: 120
ctattggaaa cacaagggg                                                19

<210> SEQ ID NO 121
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: upstream amplification primer 99-5339 for SEQ
      58,

<400> SEQUENCE: 121
acccttgtct gtatatcc                                                 18

<210> SEQ ID NO 122
<211> LENGTH: 20
<212> TYPE: DNA
<213> ORGANISM: Homo Sapiens
<220> FEATURE:
<221> NAME/KEY: primer_bind
<222> LOCATION: 1..20
<223> OTHER INFORMATION: upstream amplification primer 99-5575 for SEQ
      59,

<400> SEQUENCE: 122
gaaaaattgt ttgtgctctg                                               20

<210> SEQ ID NO 123
<211> LENGTH: 19
<212> TYPE: DNA
<213> ORGANISM: Homo Sapiens
```

```
<220> FEATURE:
<221> NAME/KEY: primer_bind
<222> LOCATION: 1..19
<223> OTHER INFORMATION: upstream amplification primer 99-619 for SEQ
      60,

<400> SEQUENCE: 123
ttccaaaccc ctacctctc                                                    19

<210> SEQ ID NO 124
<211> LENGTH: 19
<212> TYPE: DNA
<213> ORGANISM: Homo Sapiens
<220> FEATURE:
<221> NAME/KEY: primer_bind
<222> LOCATION: 1..19
<223> OTHER INFORMATION: upstream amplification primer 99-622 for SEQ
      61,

<400> SEQUENCE: 124
cctactacta cttctcttc                                                    19

<210> SEQ ID NO 125
<211> LENGTH: 21
<212> TYPE: DNA
<213> ORGANISM: Homo Sapiens
<220> FEATURE:
<221> NAME/KEY: primer_bind
<222> LOCATION: 1..21
<223> OTHER INFORMATION: upstream amplification primer 99-7183 for SEQ
      62,

<400> SEQUENCE: 125
ttaatcgtcc tccattcttc c                                                 21

<210> SEQ ID NO 126
<211> LENGTH: 21
<212> TYPE: DNA
<213> ORGANISM: Homo Sapiens
<220> FEATURE:
<221> NAME/KEY: primer_bind
<222> LOCATION: 1..21
<223> OTHER INFORMATION: upstream amplification primer 99-952 for SEQ
      63,

<400> SEQUENCE: 126
cacaaaatca taaatgacca g                                                 21

<210> SEQ ID NO 127
<211> LENGTH: 20
<212> TYPE: DNA
<213> ORGANISM: Homo Sapiens
<220> FEATURE:
<221> NAME/KEY: primer_bind
<222> LOCATION: 1..20
<223> OTHER INFORMATION: downstream amplification primer 10-102 for SEQ
      1, in complement

<400> SEQUENCE: 127
aggaagagaa acaagggctg                                                   20

<210> SEQ ID NO 128
<211> LENGTH: 20
<212> TYPE: DNA
<213> ORGANISM: Homo Sapiens
```

-continued

```
<220> FEATURE:
<221> NAME/KEY: primer_bind
<222> LOCATION: 1..20
<223> OTHER INFORMATION: downstream amplification primer 10-24 for SEQ
      2, in complement

<400> SEQUENCE: 128
cagtcaggat gggtactaag                                                20

<210> SEQ ID NO 129
<211> LENGTH: 20
<212> TYPE: DNA
<213> ORGANISM: Homo Sapiens
<220> FEATURE:
<221> NAME/KEY: primer_bind
<222> LOCATION: 1..20
<223> OTHER INFORMATION: downstream amplification primer 10-88 for SEQ
      3, in complement

<400> SEQUENCE: 129
ttacttcctt tcacctcatc                                                20

<210> SEQ ID NO 130
<211> LENGTH: 20
<212> TYPE: DNA
<213> ORGANISM: Homo Sapiens
<220> FEATURE:
<221> NAME/KEY: primer_bind
<222> LOCATION: 1..20
<223> OTHER INFORMATION: downstream amplification primer 4-14 for SEQ 4,
      in complement

<400> SEQUENCE: 130
gactgtatcc tttgatgcac                                                20

<210> SEQ ID NO 131
<211> LENGTH: 20
<212> TYPE: DNA
<213> ORGANISM: Homo Sapiens
<220> FEATURE:
<221> NAME/KEY: primer_bind
<222> LOCATION: 1..20
<223> OTHER INFORMATION: downstream amplification primer 4-20 for SEQ 5,
      in complement

<400> SEQUENCE: 131
gcataattgt gcttgactgg                                                20

<210> SEQ ID NO 132
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: downstream amplification primer 4-22 for SEQ 6,
      in complement

<400> SEQUENCE: 132
tgctgagagg agcttttg                                                  18

<210> SEQ ID NO 133
<211> LENGTH: 18
<212> TYPE: DNA
<213> ORGANISM: Homo Sapiens
```

-continued

```
<220> FEATURE:
<221> NAME/KEY: primer_bind
<222> LOCATION: 1..18
<223> OTHER INFORMATION: downstream amplification primer 4-26 for SEQ 7,
      in complement

<400> SEQUENCE: 133
tgaggactgc taggaaag                                                 18

<210> SEQ ID NO 134
<211> LENGTH: 20
<212> TYPE: DNA
<213> ORGANISM: Homo Sapiens
<220> FEATURE:
<221> NAME/KEY: primer_bind
<222> LOCATION: 1..20
<223> OTHER INFORMATION: downstream amplification primer 4-3 for SEQ 8,
      in complement

<400> SEQUENCE: 134
acaaaatcag gaacaatggg                                               20

<210> SEQ ID NO 135
<211> LENGTH: 19
<212> TYPE: DNA
<213> ORGANISM: Homo Sapiens
<220> FEATURE:
<221> NAME/KEY: primer_bind
<222> LOCATION: 1..19
<223> OTHER INFORMATION: downstream amplification primer 4-32 for SEQ 9,
      in complement

<400> SEQUENCE: 135
ctcatggaga aaagaaac                                                 19

<210> SEQ ID NO 136
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: downstream amplification primer 4-38 for SEQ 10,
      in complement

<400> SEQUENCE: 136
ttgcattttc cccccaac                                                 18

<210> SEQ ID NO 137
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: downstream amplification primer 4-4 for SEQ 11,
      in complement

<400> SEQUENCE: 137
accatttgga caatgggg                                                 18

<210> SEQ ID NO 138
<211> LENGTH: 20
<212> TYPE: DNA
<213> ORGANISM: Homo Sapiens
```

```
<220> FEATURE:
<221> NAME/KEY: primer_bind
<222> LOCATION: 1..20
<223> OTHER INFORMATION: downstream amplification primer 4-42 for SEQ
      12, in complement

<400> SEQUENCE: 138
gctcttaaac tggctctgtg                                                20

<210> SEQ ID NO 139
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: downstream amplification primer 4-43 for SEQ
      13, in complement

<400> SEQUENCE: 139
ggcatgactt cacgtttc                                                  18

<210> SEQ ID NO 140
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: downstream amplification primer 4-50 for SEQ
      14, in complement

<400> SEQUENCE: 140
aggatcttct acagtcac                                                  18

<210> SEQ ID NO 141
<211> LENGTH: 20
<212> TYPE: DNA
<213> ORGANISM: Homo Sapiens
<220> FEATURE:
<221> NAME/KEY: primer_bind
<222> LOCATION: 1..20
<223> OTHER INFORMATION: downstream amplification primer 4-52 for SEQ
      15, in complement

<400> SEQUENCE: 141
tggtagcgtt tgaaatcatc                                                20

<210> SEQ ID NO 142
<211> LENGTH: 20
<212> TYPE: DNA
<213> ORGANISM: Homo Sapiens
<220> FEATURE:
<221> NAME/KEY: primer_bind
<222> LOCATION: 1..20
<223> OTHER INFORMATION: downstream amplification primer 4-53 for SEQ
      16, in complement

<400> SEQUENCE: 142
tataagcaca aataggttcc                                                20

<210> SEQ ID NO 143
<211> LENGTH: 18
<212> TYPE: DNA
<213> ORGANISM: Homo Sapiens
```

```
<220> FEATURE:
<221> NAME/KEY: primer_bind
<222> LOCATION: 1..18
<223> OTHER INFORMATION: downstream amplification primer 4-54 for SEQ
      17, in complement

<400> SEQUENCE: 143
gaataactga ggggagtg                                                    18

<210> SEQ ID NO 144
<211> LENGTH: 19
<212> TYPE: DNA
<213> ORGANISM: Homo Sapiens
<220> FEATURE:
<221> NAME/KEY: primer_bind
<222> LOCATION: 1..19
<223> OTHER INFORMATION: downstream amplification primer 4-55 for SEQ
      18, in complement

<400> SEQUENCE: 144
gtgaatctcc ttttccaag                                                   19

<210> SEQ ID NO 145
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: downstream amplification primer 4-56 for SEQ
      19, in complement

<400> SEQUENCE: 145
ctaaggtgtt gtagacag                                                    18

<210> SEQ ID NO 146
<211> LENGTH: 20
<212> TYPE: DNA
<213> ORGANISM: Homo Sapiens
<220> FEATURE:
<221> NAME/KEY: primer_bind
<222> LOCATION: 1..20
<223> OTHER INFORMATION: downstream amplification primer 4-58 for SEQ
      20, in complement

<400> SEQUENCE: 146
cacctcgata aatcaagtcc                                                  20

<210> SEQ ID NO 147
<211> LENGTH: 20
<212> TYPE: DNA
<213> ORGANISM: Homo Sapiens
<220> FEATURE:
<221> NAME/KEY: primer_bind
<222> LOCATION: 1..20
<223> OTHER INFORMATION: downstream amplification primer 4-60 for SEQ
      21, in complement

<400> SEQUENCE: 147
gttcacttaa ttctgttgag                                                  20

<210> SEQ ID NO 148
<211> LENGTH: 20
<212> TYPE: DNA
<213> ORGANISM: Homo Sapiens
```

```
<220> FEATURE:
<221> NAME/KEY: primer_bind
<222> LOCATION: 1..20
<223> OTHER INFORMATION: downstream amplification primer 4-76 for SEQ
      22, in complement

<400> SEQUENCE: 148
gcagtatcat aagaacaggg                                                  20

<210> SEQ ID NO 149
<211> LENGTH: 20
<212> TYPE: DNA
<213> ORGANISM: Homo Sapiens
<220> FEATURE:
<221> NAME/KEY: primer_bind
<222> LOCATION: 1..20
<223> OTHER INFORMATION: downstream amplification primer 4-77 for SEQ
      23, in complement

<400> SEQUENCE: 149
ggaaaggtac tcattcatag                                                  20

<210> SEQ ID NO 150
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: downstream amplification primer 4-84 for SEQ
      24, in complement

<400> SEQUENCE: 150
cgccttttct gaaaggtg                                                    18

<210> SEQ ID NO 151
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: downstream amplification primer 4-86 for SEQ
      25, in complement

<400> SEQUENCE: 151
attttctgca cagcagcg                                                    18

<210> SEQ ID NO 152
<211> LENGTH: 19
<212> TYPE: DNA
<213> ORGANISM: Homo Sapiens
<220> FEATURE:
<221> NAME/KEY: primer_bind
<222> LOCATION: 1..19
<223> OTHER INFORMATION: downstream amplification primer 4-88 for SEQ
      26 in complement

<400> SEQUENCE: 152
tattttctag ctcttctgg                                                   19

<210> SEQ ID NO 153
<211> LENGTH: 19
<212> TYPE: DNA
<213> ORGANISM: Homo Sapiens
```

```
<220> FEATURE:
<221> NAME/KEY: primer_bind
<222> LOCATION: 1..19
<223> OTHER INFORMATION: downstream amplification primer 4-89 for SEQ
      27, in complement

<400> SEQUENCE: 153
agcaagagtg attgtaaag                                                    19

<210> SEQ ID NO 154
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: downstream amplification primer 4-9 for SEQ 28,
      in complement

<400> SEQUENCE: 154
gctgacaccc attcattc                                                     18

<210> SEQ ID NO 155
<211> LENGTH: 20
<212> TYPE: DNA
<213> ORGANISM: Homo Sapiens
<220> FEATURE:
<221> NAME/KEY: primer_bind
<222> LOCATION: 1..20
<223> OTHER INFORMATION: downstream amplification primer 5-11 for SEQ
      29, in complement

<400> SEQUENCE: 155
gatgtcagtc aacatcagtc                                                   20

<210> SEQ ID NO 156
<211> LENGTH: 20
<212> TYPE: DNA
<213> ORGANISM: Homo Sapiens
<220> FEATURE:
<221> NAME/KEY: primer_bind
<222> LOCATION: 1..20
<223> OTHER INFORMATION: downstream amplification primer 5-14 for SEQ
      30, in complement

<400> SEQUENCE: 156
ctccacgtaa aatgaaaatg                                                   20

<210> SEQ ID NO 157
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: downstream amplification primer 5-15 for SEQ
      31, in complement

<400> SEQUENCE: 157
atgaacccag ttccattg                                                     18

<210> SEQ ID NO 158
<211> LENGTH: 20
<212> TYPE: DNA
<213> ORGANISM: Homo Sapiens
```

-continued

<220> FEATURE:
<221> NAME/KEY: primer_bind
<222> LOCATION: 1..20
<223> OTHER INFORMATION: downstream amplification primer 5-2 for SEQ
      32, in complement

<400> SEQUENCE: 158
acagcaatga aataaatccc                                              20

<210> SEQ ID NO 159
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: downstream amplification primer 5-3 for SEQ 33,
      in complement

<400> SEQUENCE: 159
tatttaggtg ccttcctg                                                18

<210> SEQ ID NO 160
<211> LENGTH: 21
<212> TYPE: DNA
<213> ORGANISM: Homo Sapiens
<220> FEATURE:
<221> NAME/KEY: primer_bind
<222> LOCATION: 1..21
<223> OTHER INFORMATION: downstream amplification primer 5-5 for SEQ 34,
      in complement

<400> SEQUENCE: 160
attttcaaaa acccagcctt c                                            21

<210> SEQ ID NO 161
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: downstream amplification primer 5-7 for SEQ 35,
      in complement

<400> SEQUENCE: 161
cacaatctaa ccacctcc                                                18

<210> SEQ ID NO 162
<211> LENGTH: 19
<212> TYPE: DNA
<213> ORGANISM: Homo Sapiens
<220> FEATURE:
<221> NAME/KEY: primer_bind
<222> LOCATION: 1..19
<223> OTHER INFORMATION: downstream amplification primer 99-1051 for SEQ
      36, in complement

<400> SEQUENCE: 162
cctgggttct gacctttg                                                19

<210> SEQ ID NO 163
<211> LENGTH: 20
<212> TYPE: DNA
<213> ORGANISM: Homo Sapiens

```
<220> FEATURE:
<221> NAME/KEY: primer_bind
<222> LOCATION: 1..20
<223> OTHER INFORMATION: downstream amplification primer 99-1182 for SEQ
      37, in complement

<400> SEQUENCE: 163
ccattcatat ttcactccac                                                   20

<210> SEQ ID NO 164
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: downstream amplification primer 99-123 for SEQ
      38, in complement

<400> SEQUENCE: 164
tattcagaaa ggagtggg                                                     18

<210> SEQ ID NO 165
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: downstream amplification primer 99-128 for SEQ
      39, in complement

<400> SEQUENCE: 165
agagcgttct tgcctttc                                                     18

<210> SEQ ID NO 166
<211> LENGTH: 19
<212> TYPE: DNA
<213> ORGANISM: Homo Sapiens
<220> FEATURE:
<221> NAME/KEY: primer_bind
<222> LOCATION: 1..19
<223> OTHER INFORMATION: downstream amplification primer 99-1453 for SEQ
      40, in complement

<400> SEQUENCE: 166
ctggaggtat tagttgatg                                                    19

<210> SEQ ID NO 167
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: downstream amplification primer 99-1480 for SEQ
      41, in complement

<400> SEQUENCE: 167
ggtgacaggt aaagaaac                                                     18

<210> SEQ ID NO 168
<211> LENGTH: 19
<212> TYPE: DNA
<213> ORGANISM: Homo Sapiens
```

-continued

```
<220> FEATURE:
<221> NAME/KEY: primer_bind
<222> LOCATION: 1..19
<223> OTHER INFORMATION: downstream amplification primer 99-1490 for SEQ
      42, in complement

<400> SEQUENCE: 168
gaaaacaatc aagctctgg                                                19

<210> SEQ ID NO 169
<211> LENGTH: 19
<212> TYPE: DNA
<213> ORGANISM: Homo Sapiens
<220> FEATURE:
<221> NAME/KEY: primer_bind
<222> LOCATION: 1..19
<223> OTHER INFORMATION: downstream amplification primer 99-1493 for SEQ
      43, in complement

<400> SEQUENCE: 169
cctttatatc cttggagtc                                                19

<210> SEQ ID NO 170
<211> LENGTH: 21
<212> TYPE: DNA
<213> ORGANISM: Homo Sapiens
<220> FEATURE:
<221> NAME/KEY: primer_bind
<222> LOCATION: 1..21
<223> OTHER INFORMATION: downstream amplification primer 99-1572 for SEQ
      44, in complement

<400> SEQUENCE: 170
gattattgat aaagtcagga g                                             21

<210> SEQ ID NO 171
<211> LENGTH: 19
<212> TYPE: DNA
<213> ORGANISM: Homo Sapiens
<220> FEATURE:
<221> NAME/KEY: primer_bind
<222> LOCATION: 1..19
<223> OTHER INFORMATION: downstream amplification primer 99-1582 for SEQ
      45, in complement

<400> SEQUENCE: 171
cagagtttaa ttgagcaag                                                19

<210> SEQ ID NO 172
<211> LENGTH: 20
<212> TYPE: DNA
<213> ORGANISM: Homo Sapiens
<220> FEATURE:
<221> NAME/KEY: primer_bind
<222> LOCATION: 1..20
<223> OTHER INFORMATION: downstream amplification primer 99-1585 for SEQ
      46, in complement

<400> SEQUENCE: 172
ttctgagata ggagaaaaac                                               20

<210> SEQ ID NO 173
<211> LENGTH: 20
<212> TYPE: DNA
<213> ORGANISM: Homo Sapiens
```

-continued

```
<220> FEATURE:
<221> NAME/KEY: primer_bind
<222> LOCATION: 1..20
<223> OTHER INFORMATION: downstream amplification primer 99-1591 for SEQ
      47, in complement

<400> SEQUENCE: 173
tacttcaccc atcataagac                                              20

<210> SEQ ID NO 174
<211> LENGTH: 20
<212> TYPE: DNA
<213> ORGANISM: Homo Sapiens
<220> FEATURE:
<221> NAME/KEY: primer_bind
<222> LOCATION: 1..20
<223> OTHER INFORMATION: downstream amplification primer 99-1602 for SEQ
      48, in complement

<400> SEQUENCE: 174
gtggtaggtt aaaaaatcag                                              20

<210> SEQ ID NO 175
<211> LENGTH: 21
<212> TYPE: DNA
<213> ORGANISM: Homo Sapiens
<220> FEATURE:
<221> NAME/KEY: primer_bind
<222> LOCATION: 1..21
<223> OTHER INFORMATION: downstream amplification primer 99-1605 for
      SEQ 49, in complement

<400> SEQUENCE: 175
ggaaagatga cttggaaaat g                                            21

<210> SEQ ID NO 176
<211> LENGTH: 21
<212> TYPE: DNA
<213> ORGANISM: Homo Sapiens
<220> FEATURE:
<221> NAME/KEY: primer_bind
<222> LOCATION: 1..21
<223> OTHER INFORMATION: downstream amplification primer 99-1607 for SEQ
      50, in complement

<400> SEQUENCE: 176
aaaacaggtg aaagataagg g                                            21

<210> SEQ ID NO 177
<211> LENGTH: 19
<212> TYPE: DNA
<213> ORGANISM: Homo Sapiens
<220> FEATURE:
<221> NAME/KEY: primer_bind
<222> LOCATION: 1..19
<223> OTHER INFORMATION: downstream amplification primer 99-2222 for SEQ
      51, in complement

<400> SEQUENCE: 177
agggagggaa ccatgtaag                                               19

<210> SEQ ID NO 178
<211> LENGTH: 21
<212> TYPE: DNA
<213> ORGANISM: Homo Sapiens
```

```
-continued

<220> FEATURE:
<221> NAME/KEY: primer_bind
<222> LOCATION: 1..21
<223> OTHER INFORMATION: downstream amplification primer 99-2797 for SEQ
      52, in complement

<400> SEQUENCE: 178 gggtggttg aaatcattag g                                          21

<210> SEQ ID NO 179
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: downstream amplification primer 99-2914 for SEQ
      53, in complement

<400> SEQUENCE: 179 agggtgaat tttcgttg                                              18

<210> SEQ ID NO 180
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: downstream amplification primer 99-3047 for SEQ
      54, in complement

<400> SEQUENCE: 180
cataacagtc agacatgg                                             18

<210> SEQ ID NO 181
<211> LENGTH: 21
<212> TYPE: DNA
<213> ORGANISM: Homo Sapiens
<220> FEATURE:
<221> NAME/KEY: primer_bind
<222> LOCATION: 1..21
<223> OTHER INFORMATION: downstream amplification primer 99-3484 for SEQ
      55, in complement

<400> SEQUENCE: 181
catgagaata gccttgtctc c                                         21

<210> SEQ ID NO 182
<211> LENGTH: 21
<212> TYPE: DNA
<213> ORGANISM: Homo Sapiens
<220> FEATURE:
<221> NAME/KEY: primer_bind
<222> LOCATION: 1..21
<223> OTHER INFORMATION: downstream amplification primer 99-4182 for SEQ
      56, in complement

<400> SEQUENCE: 182
gcattgtttt aatctcatag g                                         21

<210> SEQ ID NO 183
<211> LENGTH: 21
<212> TYPE: DNA
<213> ORGANISM: Homo Sapiens
```

-continued

```
<220> FEATURE:
<221> NAME/KEY: primer_bind
<222> LOCATION: 1..21
<223> OTHER INFORMATION: downstream amplification primer 99-4202 for SEQ
      57, in complement

<400> SEQUENCE: 183
tggaatactc aatgttgctg g                                           21

<210> SEQ ID NO 184
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: downstream amplification primer 99-5339 for SEQ
      58, in complement

<400> SEQUENCE: 184
gaatcctgct tcattgcc                                               18

<210> SEQ ID NO 185
<211> LENGTH: 21
<212> TYPE: DNA
<213> ORGANISM: Homo Sapiens
<220> FEATURE:
<221> NAME/KEY: primer_bind
<222> LOCATION: 1..21
<223> OTHER INFORMATION: downstream amplification primer 99-5575 for SEQ
      59, in complement

<400> SEQUENCE: 185
ttaagagaga atagactttg g                                           21

<210> SEQ ID NO 186
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: downstream amplification primer 99-619 for SEQ
      60, in complement

<400> SEQUENCE: 186
atacctctgt gccattac                                               18

<210> SEQ ID NO 187
<211> LENGTH: 21
<212> TYPE: DNA
<213> ORGANISM: Homo Sapiens
<220> FEATURE:
<221> NAME/KEY: primer_bind
<222> LOCATION: 1..21
<223> OTHER INFORMATION: downstream amplification primer 99-622 for SEQ
      61, in complement

<400> SEQUENCE: 187
ctatcttcaa acataagacc c                                           21

<210> SEQ ID NO 188
<211> LENGTH: 21
<212> TYPE: DNA
<213> ORGANISM: Homo Sapiens
```

-continued

```
<220> FEATURE:
<221> NAME/KEY: primer_bind
<222> LOCATION: 1..21
<223> OTHER INFORMATION: downstream amplification primer 99-7183 for SEQ
      62, in complement

<400> SEQUENCE: 188
aaaaaaccag caaactgtgc c                                              21

<210> SEQ ID NO 189
<211> LENGTH: 18
<212> TYPE: DNA
<213> ORGANISM: Homo Sapiens
<220> FEATURE:
<221> NAME/KEY: primer_bind
<222> LOCATION: 1..18
<223> OTHER INFORMATION: downstream amplification primer 99-952 for SEQ
      63, in complement

<400> SEQUENCE: 189
aacagtacac acttgggc                                                  18
```

METHODS OF GENETIC CLUSTER ANALYSIS AND USES THEREOF

RELATED APPLICATIONS

The applications claims priority to U.S. Provisional Patent Application No. 60/161,231 entitled "Methods of Genetic Cluster Analysis and Uses Thereof" by Schork and Skierczynski, filed Oct. 22, 1999 and U.S. Provisional Patent Application No. 60/216,897 entitled "Methods of Genetic Cluster Analysis and Uses Thereof" by Schork and Skierczynski, filed Jul. 7, 2000, both of which are hereby incorporated by reference herein in their entirety including and figures, drawings, or tables.

FIELD OF THE INVENTION

The present invention is in the field of applied genomics, and is primarily directed to methods of genetic cluster analysis to determine the homogeneity and/or heterogeneity of a population or sub-population.

BACKGROUND OF THE INVENTION

The following discussion is meant to aid in the understanding of the invention, but is not intended to, and is not admitted to, describe prior art to the invention.

Populations can vary considerably with respect to the number and frequency of genetic variants that they possess. Analogously, or consequently, individuals within such populations can vary considerably in terms of the composition of their genomes. Both of these facts contribute to the tremendous phenotypic variation exhibited among individuals within and between populations.

Various genetic systems and analyses have been used to assess the relationship between genes and phenotype (Lander & Schork, Science 265:2037–2048, 1994). Fundamental to such analyses is the assumption that the sample of individuals with (and/or without) a particular phenotype chosen for study is "homogenous" with respect to the cause of the phenotype (i.e. the individuals in the sample have (or don't have) the phenotype for some reason). When this is not the case, a relevant study of the relationship between the phenotype and its determinant(s) is unlikely to be successful. Assessment of the "similarity" of individuals in a sample with respect to genetic backgrounds and molecular profile may thus provide a useful measure of this homogeneity (Curnow, J. Agricul., Biol., and Environ Stat. 3:347–358, 1998). Such homogeneity assessment can be of value to any study, but depends on the identification of individuals with certain features based on some distinguishing genetic characteristics, such as forensic applications.

Analyses assessing the similarity in the genetic profiles of individuals have been pursued. For example, polymorphic microsatellites (primarily CA repeats) have been used to construct trees of human individuals that reflect their geographic origin (Bowcock et al., Nature 368:455–457, 1994), and to study the genetic variability within and between cattle breeds (Ciampolini, et al, J. Anim. Sci. 73:3259–3268, 1995). RFLP genotypes have been used to construct trees of individuals of different ethnicities (Mountain and Cavalli-Sforza, Am. J. Hum. Genet. 61:705–718, 1997). Random amplified polymorphic DNA (RAPD) markers have been used to compute genetic similarity coefficients (Lamboy, PCR Methods and Applications 4:31–37, 1994), and to compare phenotype and genotype in plants (Jasienski, et al, Heredity 78:176–181, 1997).

However, these analyses often rely on a priori knowledge of the groups to which the individuals belong. Many do not permit the determination in the absence of a priori knowledge of which, and to what degree, different populations may have contributed to the genetic variation within a pool or sample of individuals. However, in the large majority of cases, individuals sampled from a population represent an "admixture" of genes from several populations. These populations are reflected in the genetic profiles of individuals and hence can defy population segregation based on traditional markers such as skin color and/or self-reported ethnic affiliation. Therefore, methods of analysis are needed to accurately determine the existence of clusters of genetically similar individuals, absent phenotypic (ethnic, for example) information. As noted previously, knowledge of the homogeneity or heterogeneity of a population can be important under many circumstances including forensics and population-based studies.

In forensics, DNA fingerprinting requires the computation of 'match probabilities' between the suspect and the DNA obtained on a victim. Match probabilities are often computed relative to a database of non-suspect DNA. The utility of the DNA contributed by non-suspects will be influenced by the amount of genetic heterogeneity among the non-suspects (Jin & Chalraborty, Heredity 74:274–285, 1995; Sawyer et al, Am. J. Hum. Genet. 59:272–274, 1996; Tomsey et al., J. Forensic Sci. 44:385–388, 1999). Thus, determining the heterogeneity of the non-suspect population sample (on its own and compared with the DNA obtained on a victim) is important for a meaningful control.

In addition, many population-based studies, such as large clinical trials, case-control studies of disease risk factors, and gene mapping studies, assume that the populations under study are relatively homogenous genetically. When this assumption is erroneous, false inferences about the efficacy of a compound or the role of a particular risk factor in disease pathogenesis, for example, can result. Assessment of the heterogeneity of the population avoids misleading results.

SUMMARY OF THE INVENTION

A basic assumption is that genetic similarity should correlate with phenotypic similarity; there should be a relationship between genotype and phenotype at all relevant loci. The validity of this assumption for a given population has important implications for the accuracy and the understanding of the results of a given study, for example the efficacy of a compound or the role of a particular risk factor in disease pathogenesis, among others.

A corollary to this assumption is that a given population is homogeneous; the patient and control populations for instance should be genetically different from each other at loci which influence the trait studied, but should otherwise be a homogenous population. However, up to now there has been no good way to test the heterogeneity or homogeneity of a population at the genetic level; the assessment has been made at the phenotypic levels. The methods of the invention allow the determination of the heterogeneity or homogeneity of a population at the genetic level.

In a first aspect, the invention features methods of clustering members of a sample, comprising: a) identifying traits to be measured; b) assigning values to said traits; c) assigning weights based on the frequency of selected trait values in said sample; d) forming an ordered set of similarity data by determining the similarity between pairs of members of said sample using said trait values and said weights; e) calculating an ordered set of distance data from said ordered set of similarity data; f) applying a hierarchical clustering algorithm to said distance matrix; g) determining the optimal number of clusters based on the results of said hierarchical clustering algorithm, wherein said optimal number of clusters is found where the average pairwise intracluster similarity for two parent clusters is larger than the average pairwise intracluster similarity for a new cluster; h) applying a non-hierarchical clustering algorithm to said ordered set of similarity data using said optimal number of clusters; i) determining the relatedness between pairs of homozygous pairs by performing a paired-pair analysis on the clusters resulting from said non-hierarchical clustering algorithm, wherein the homozygous loci of two pairs are compared pairwise to determine whether the pairs share the same homozygous alleles on the same loci; j) summing said paired-pair comparison for one pair versus all pairs in a cluster; k) computing the average sum of said paired-pair comparison for all pairs in said cluster; l) assigning values to the homozygous relatedness of each member of a pair to all homozygotes in said cluster based on whether said sum for one pair is greater than or equal to said average sum of all pairs, or whether said sum for one pair is less than said average sum for all pairs; m) comparing the number of times said sum for one pair is greater than or equal to said average sum of all pairs with the number of times said sum for one pair is less than said average sum for all pairs for each individual in said cluster; and n) dividing said cluster into a first cluster and a second cluster if there is: a first group of members of said cluster wherein said number of times said sum of one pair is less than said average sum of pairs is greater than or equal to said number of times said sum for one pair is greater than or equal to said average sum for all pairs, and a second group of members of said cluster wherein said number of times said sun of one pair is less than said average sum of pairs is less than said number of times said sum for one pair is greater than or equal to said average sum for all pairs, and wherein said first group of members are placed into said first cluster and said second group of members are placed into said second cluster.

In preferred embodiments of the invention, said traits are genetic loci and said values are assigned to said traits based on the alleles of said genetic loci. Preferably, said values are: 0 when a pair of members share no common allele; 1 when a pair of members share a common allele; and 2 when a pair of members share two common alleles. Preferably, said weights are assigned based on: sharing rare alleles between a pair of members; and sharing a homozygous genotype between a pair of members.

In other preferred embodiments, said ordered set of similarity data is present in a similarity matrix. Preferably, said similarity matrix is formed based on the pairwise similarity measure:

$$S_{ij} = \sum_{k=1}^{L} \frac{a_{k,ij} \cdot w_{r,k,ij} \cdot w_{h,kij}}{2L}$$

where i and j denote the particular members;
where k denotes a particular locus;
where L denotes the total number of loci;
where $a_{k,ij}$ equals 0 for locus k when members i and j share no common allele,
   $a_{k,ij}$ equals 1 for locus k when members i and j have one common allele, and
   $a_{k,ij}$ equals 2 for locus k when members i and j have two common alleles; where
$w_{r,k,ij}$ denotes a weight function for sharing rare alleles; and
where $w_{h,k,ij}$ denotes a weight function for sharing a homozygous genotype.

In other preferred embodiments, said ordered set of distance data is present in a distance matrix. Preferably, said distance matrix is generated using distances selected from the group consisting of Euclidean squared distance, Euclidean distance, absolute distance, and correlation coefficient. Most preferably, said distance matrix is generated using Euclidean squared distance.

In yet other preferred embodiments, said hierarchical clustering algorithm produces a dendrogram based on calculations selected from the group consisting of minimum variance, nearest neighbor, furthest neighbor, group average, and median computations. Preferably, said hierarchical clustering algorithm produces a dendrogram based on minimum variance calculations.

In still other preferred embodiments, said non-hierarchical clustering algorithm uses K-means clustering. Preferably, said K-means clustering uses classifiers selected from the group consisting of sum of squares, nearest neighbor method, weighted nearest neighbor method, and pseudo nearest neighbor combined classifier. Most preferably, said classifier is sum of squares.

A second aspect of the invention features methods of determining the presence of clusters in a sample, comprising: a) assigning weights to selected trait values of members of said sample based on the frequency of said selected trait values in said sample; b) forming an ordered set of similarity data by determining the similarity between pairs of members of said sample using said weights; and c) applying a clustering algorithm to said ordered set of similarity data.

In preferred embodiments of the invention, said weights are assigned based on: sharing rare alleles between a pair of members; and sharing a homozygous genotype between a pair of members.

In other preferred embodiments of the invention, said ordered set of similarity data is present in a similarity matrix. Preferably, said similarity matrix is formed based on the pairwise similarity measure:

$$S_{ij} = \sum_{k=1}^{L} \frac{a_{k,ij} \cdot w_{r,k,ij} \cdot w_{h,kij}}{2L}$$

where i and j denote the particular members;
where k denotes a particular locus;
where L denotes the total number of loci;
where $a_{k,ij}$ equals 0 for locus k when members i and j share no common allele,
   $a_{k,ij}$ equals 1 for locus k when members i and j have one common allele, and
   $a_{k,ij}$ equals 2 for locus k when members i and j have two common alleles; where
$w_{r,k,ij}$ denotes a weight function for sharing rare alleles; and
where $w_{h,k,ij}$ denotes a weight function for sharing a homozygous genotype.

In other preferred embodiments, the invention further comprises calculating an ordered set of distance data from said ordered set of similarity data. Preferably, said ordered set of distance data is present in a distance matrix. Preferably, said distance matrix is generated using distances selected from the group consisting of Euclidean squared distance, Euclidean distance, absolute distance, and correlation coefficient. Most preferably, said distance matrix is generated using Euclidean squared distance.

In still other preferred embodiments, said clustering algorithm is a hierarchical clustering algorithm. Preferably, said hierarchical clustering algorithm produces a dendrogram based on calculations selected from the group consisting of minimum variance, nearest neighbor, furthest neighbor, group average, and median computations. Most preferably, said hierarchical clustering algorithm produces a dendrogram based on minimum variance calculations.

In yet other preferred embodiments, said clustering algorithm is a non-hierarchical clustering algorithm. Preferably, said non-hierachical clustering algorithm uses K-means clustering. Preferably, said K-means clustering uses classifiers selected from the group consisting of sum of squares, nearest neighbor method, weighted nearest neighbor method, and pseudo nearest neighbor combined classifier. Most preferably, said classifier is sum of squares.

A third aspect of the invention features methods of determining the number of clusters in a sample, comprising: a) applying a hierarchical clustering algorithm to the members of said sample; and b) determining the optimal number of clusters based on the results of said hierarchical clustering algorithm, wherein said optimal number of clusters is found where the average pairwise intracluster similarity for two parent clusters is larger than the average pairwise intracluster similarity for a new cluster.

A fourth aspect of the invention features methods of clustering members of a sample, comprising: a) applying a non-hierarchical clustering algorithm to said sample; b) determining the relatedness between pairs of homozygous pairs by performing a paired-pair analysis on the clusters resulting from said non-hierarchical clustering algorithm, wherein the homozygous loci of two pairs are compared pairwise to determine whether the pairs share the same homozygous alleles on the same loci; c) summing said paired-pair comparison for one pair versus all pairs in a cluster; d) computing the average sum of said paired-pair comparison for all pairs in said cluster; e) assigning values to the homozygous relatedness of each individual in a pair to all homozygotes in said cluster based on whether said sum for one pair is greater than or equal to said average sum of all pairs, or whether said sum for one pair is less than said average sum for all pairs; f) comparing the number of times said sum for one pair is greater than or equal to said average sum of all pairs with the number of times said sum for one pair is less than said average sum for all pairs for each individual in said cluster; and g) dividing said cluster into a first cluster and a second cluster if there is: a first group of individuals within said cluster wherein said number of times said sum of one pair is less than said average sum of pairs is greater than or equal to said number of times said sum for one pair is greater than or equal to said average sum for all pairs, and a second group of individuals within said cluster wherein said number of times said sum of one pair is less than said average sum of pairs is less than said number of times said sum for one pair is greater than or equal to said average sum for all pairs, and wherein said first group of individuals are placed into said first cluster and said second group of individuals are placed into said second cluster.

In a fifth aspect, the invention features a method of clustering members of a sample, comprising: applying a hierarchical clustering algorithm to said members of said sample; determining the optimal number of clusters based on the results of said hierarchical clustering algorithm; and distributing said members of said sample into said optimal number of clusters using non-hierarchical clustering. Preferably, said optimal number of clusters is found where the average pairwise intracluster similarity for two parent clusters is larger than the average pairwise intracluster similarity for a new cluster.

In preferred embodiments, this method of clustering further comprises: applying paired-pair analysis to said members in said optimal number of clusters to determine whether said clusters should be further divided; and distributing said members into additional clusters based on the results of said paired-pair analysis. Preferably, said paired-pair analysis compares the homozygousm or heterozygous loci of pairs pairwise.

In other preferred embodiments, this method of clustering further comprises constructing a similarity matrix prior to said applying step. Preferably, said similarity matrix is formed based on a pairwise similarity measure. Preferably, said pairwise similarity measure is of values for genetic loci.

In other preferred embodiments, this method of clustering further comprises constructing a distance matrix from said similarity matrix prior to said applying step.

In a sixth aspect, the invention features a method of determining the optimal number of clusters of members in a sample, comprising: applying a hierarchical clustering algorithm to said members of said sample; and determining the optimal number of clusters based on the results of said hierarchical clustering algorithm Preferably, said optimal number of clusters is found where the average pairwise intracluster similarity for two parent clusters is larger than the average pairwise intracluster similarity for a new cluster.

In a seventh aspect, the invention features a method of clustering members of a sample, comprising: applying a non-hierarchical clustering algorithm to said sample; applying paired-pair analysis to pairs of homozygous pairs in any clusters resulting from said non-hierarchical clustering algorithm to determine whether said non-hierarchical clusters should be further divided; and distributing said members into additional clusters based on the results of said paired-pair analysis. Preferably, said paired-pair analysis compares the homozygous or heterozygous loci of pairs pairwise.

In an eighth aspect, the invention features a computer system for determining clusters of members in a sample, comprising: First instructions for applying a hierarchical clustering algorithm to said members of said sample; Second instructions for determining the optimal number of clusters based on the results of said hierarchical clustering algorithm; and Third instructions for distributing said members of said sample into said optimal number of clusters using non-hierarchical clustering. Preferably, said optimal number of clusters is found where the average pairwise intracluster similarity for two parent clusters is larger than the average pairwise intracluster similarity for a new cluster.

In preferred embodiments of this computer system, it further comprises Fourth instructions for applying paired-pair analysis to said members of said optimal number of clusters to determine whether said clusters should be further divided; and Fifth instructions for distributing said members into additional clusters based on the results of said paired-pair analysis. Preferably, said paired-pair analysis compares the homozygous or heterozygous loci of pairs pairwise.

In preferred embodiments of this computer system, it further comprises sixth instructions for constructing a similarity matrix prior to said applying step. Preferably, said similarity matrix is formed based on a pairwise similarity measure. Preferably, said pairwise similarity measure is of values for genetic loci.

In other preferred embodiments of this computer system, it further comprises seventh instructions for constructing a distance matrix from said similarity matrix prior to said applying step.

In a ninth aspect, the invention features a computer system for determining the optimal number of clusters in a sample, comprising: a first module configured to apply a hierarchical clustering algorithm to the members of said sample; and a second module configured to determine the optimal number of clusters based on the results of said hierarchical clustering algorithm. Preferably, said optimal number of clusters is found where the average pairwise intracluster similarity for two parent clusters is larger than the average pairwise intracluster similarity for a new cluster.

In a tenth aspect, the invention features a computer system for clustering members of a sample, comprising: First instructions for applying a non-hierarchical clustering algorithm to said sample; Second instructions for applying paired-pair analysis to pairs of homozygous pairs in any clusters resulting from said non-hierarchical clustering algorithm to determine whether said non-hierarchical clusters should be further divided; and Third instructions for distribution of said members into additional clusters based on the results of said paired-pair analysis. Preferably, said paired-pair analysis compares the homozygous or heterozygous loci of pairs pairwise.

In an eleventh aspect, the invention features a programmed storage device comprising instructions that when executed perform a method for clustering members of a sample, comprising: applying a hierarchical clustering algorithm to said members of said sample; determining the optimal number of clusters based on the results of said hierarchical clustering algorithm; and distributing said members of said sample into said optimal number of clusters using non-hierarchical clustering. Preferably, said optimal number of clusters is found where the average pairwise intracluster similarity for two parent clusters is larger than the average pairwise intracluster similarity for a new cluster.

In preferred embodiments, the programmed storage device further comprises instructions that when executed apply paired-pair analysis to said members of said optimal number of clusters to determine whether said clusters should be further divided; and distributing said members into additional clusters based on the results of said paired-pair analysis. Preferably, said paired-pair analysis compares the homozygous or heterozygous loci of pairs pairwise.

In preferred embodiments, the programmed storage device further comprises instructions that when executed construct a similarity matrix prior to said applying step. Preferably, said similarity matrix is formed based on a pairwise similarity measure. Preferably, said pairwise similarity measure is of values for genetic loci.

In preferred embodiments, the programmed storage device further comprises instructions that when executed construct a distance matrix from said similarity matrix prior to said applying step.

In a twelfth aspect, the invention features a programmed storage device comprising instructions that when executed perform a method for determining the number of clusters in a sample, comprising: applying a hierarchical clustering algorithm to the members of said sample; and determining the optimal number of clusters based on the results of said hierarchical clustering algorithm. Preferably, said optimal number of clusters is found where the average pairwise intracluster similarity for two parent clusters is larger than the average pairwise intracluster similarity for a new cluster.

In a thirteenth aspect, the invention features a programmed storage device comprising instructions that when executed perform a method for clustering members of a sample, comprising: applying a non-hierarchical clustering algorithm to said sample; applying paired-pair analysis to pairs of homozygous pairs in any clusters resulting from said non-hierarchical clustering algorithm to determine whether said non-hierarchical clusters should be further divided; and distributing said members into additional clusters based on the results of said paired-pair analysis. Preferably, said paired-pair analysis compares the homozygous or heterozygous loci of pairs pairwise.

Additional embodiments are set forth in the Detailed Description of the Invention, in the Implementation of the Methods of the Invention section, and in the Examples.

BRIEF DESCRIPTION OF THE DRAWINGS

FIG. 10 shows the information for Cluster 1 and Cluster 2 (from FIGS. 2 and 3, respectively). FIG. 11 shows the information for Cluster 3 and Cluster 4 (FIGS. 4 and 5, respectively). FIG. 12 shows the information for Cluster 5 and Cluster 6 (FIGS. 6 and 7, respectively).

FIG. 15 shows the analysis for Cluster 1, Cluster 2, and Cluster 3. FIG. 16 shows the analysis for Cluster 4, Cluster 5, and Cluster 6. FIG. 16 shows the analysis for Cluster 7 and Cluster 8.

DETAILED DESCRIPTION OF THE INVENTION

Figure 1:
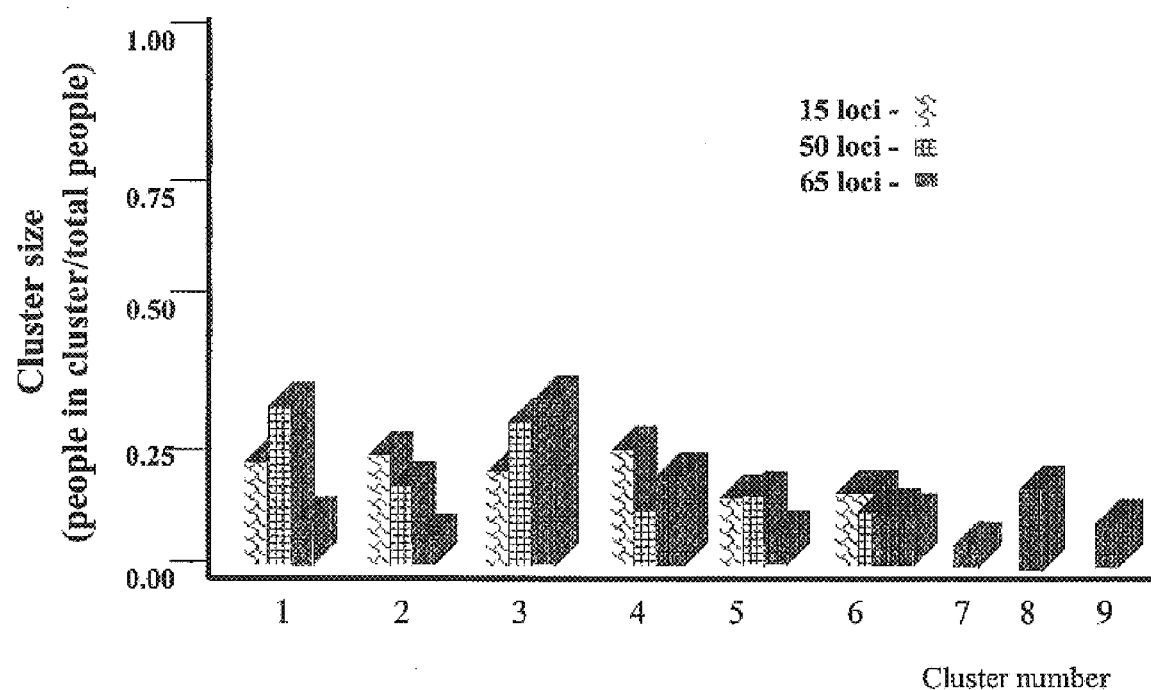
FIG. 1 shows a graph of the optimal number of clusters for 475 ethnically diverse individuals using the genetic clustering analysis of the invention based on SNP genotyping at 15 loci, 50 loci and 65 loci.
Figure 2:
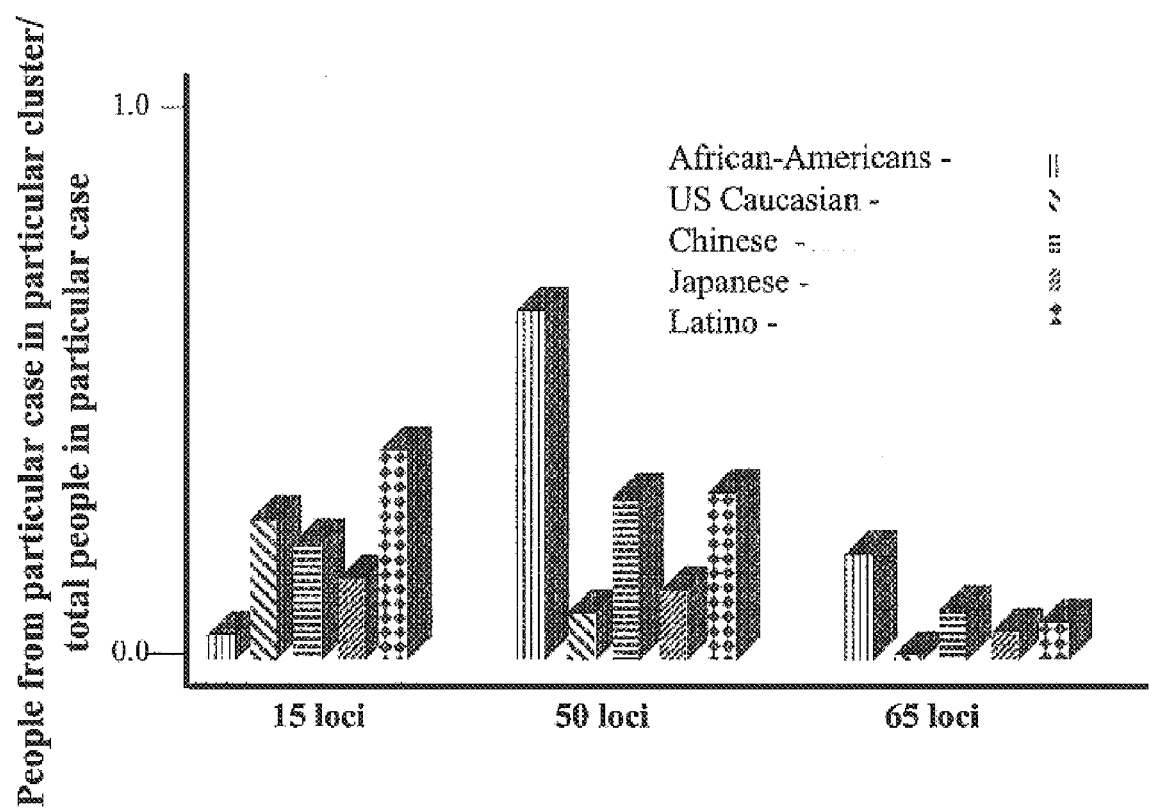
FIG. 2 shows a bar graph of the ethnic affiliation of each individual within Cluster 1 for the clustering analysis performed with 15, 50, and 65 loci.
Figure 3:
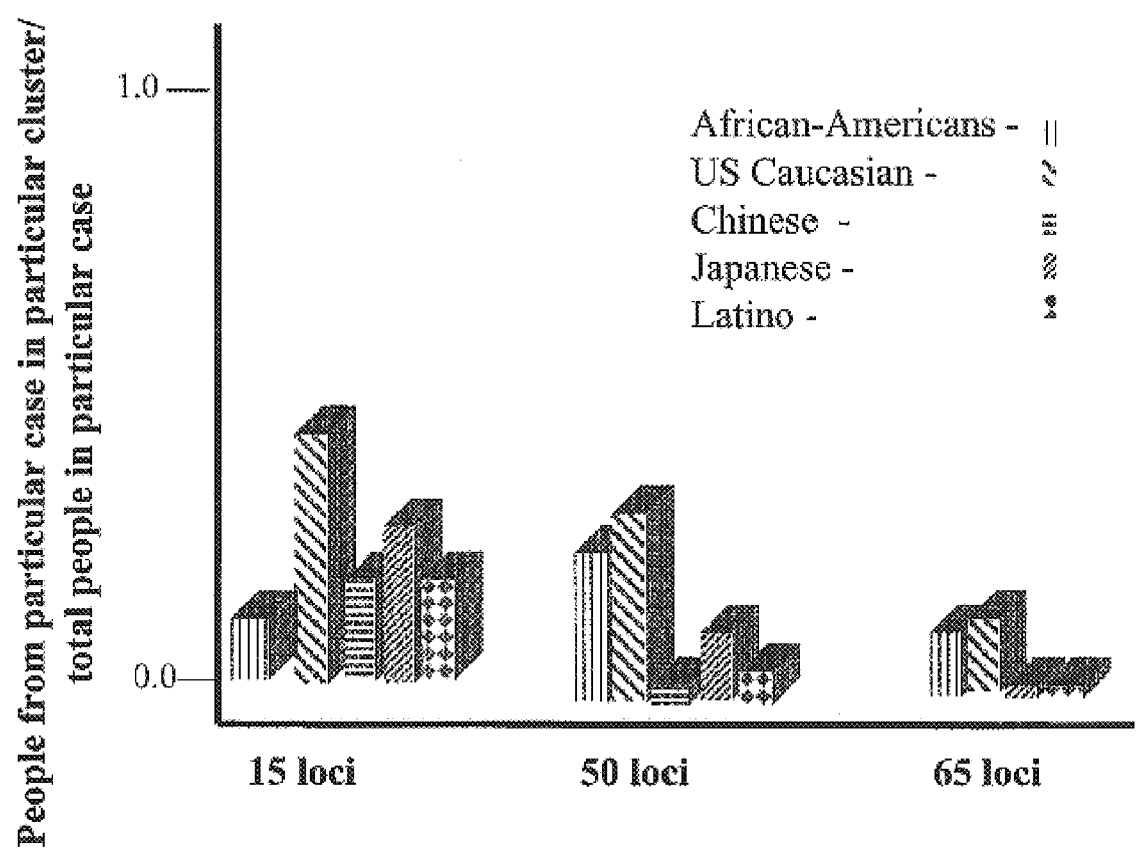
FIG. 3 shows a bar graph of the ethnic affiliation of each individual within Cluster 2 for the clustering analysis performed with 15, 50, and 65 loci.
Figure 4:
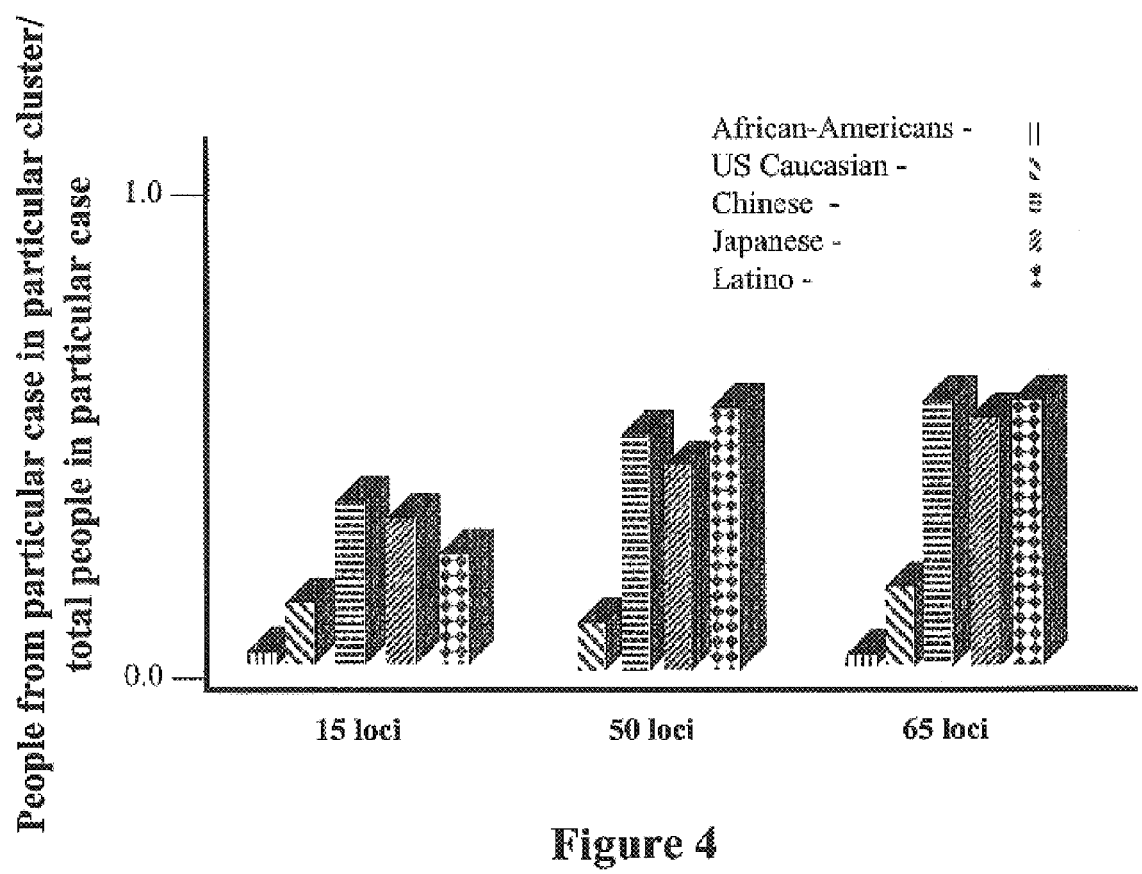
FIG. 4 shows a bar graph of the ethnic affiliation of each individual within Cluster 3 for the clustering analysis performed with 15, 50, and 65 loci.
Figure 5:
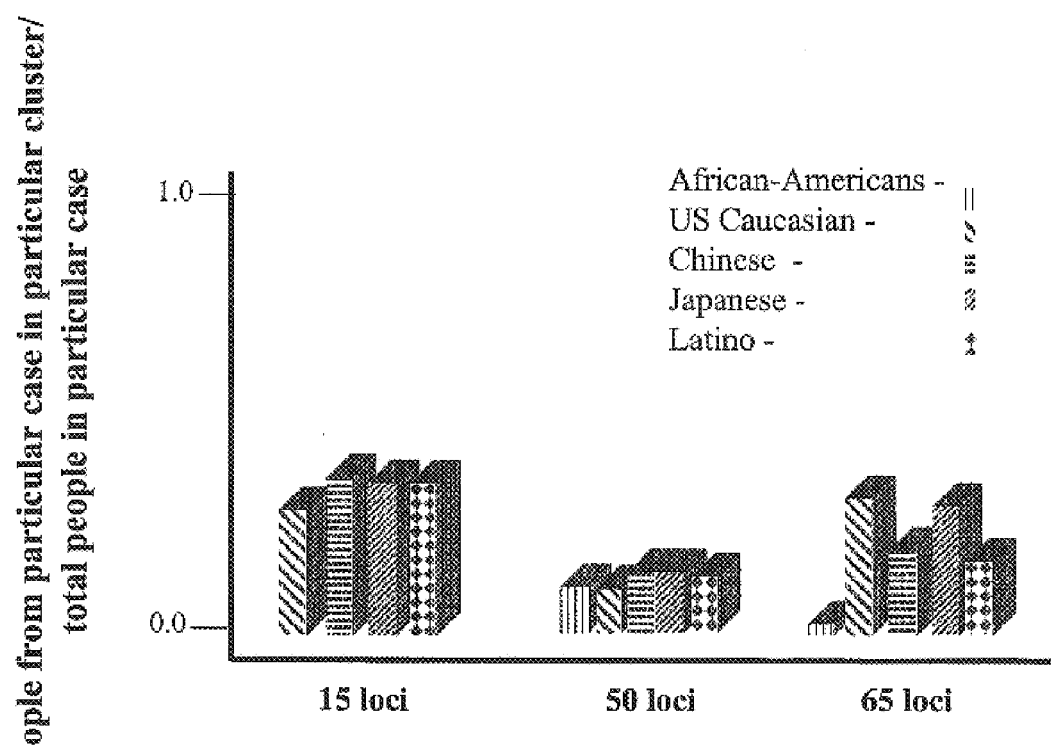
FIG. 5 shows a bar graph of the ethnic affiliation of each individual within Cluster 4 for the clustering analysis performed with 15, 50, and 65 loci.
Figure 6:
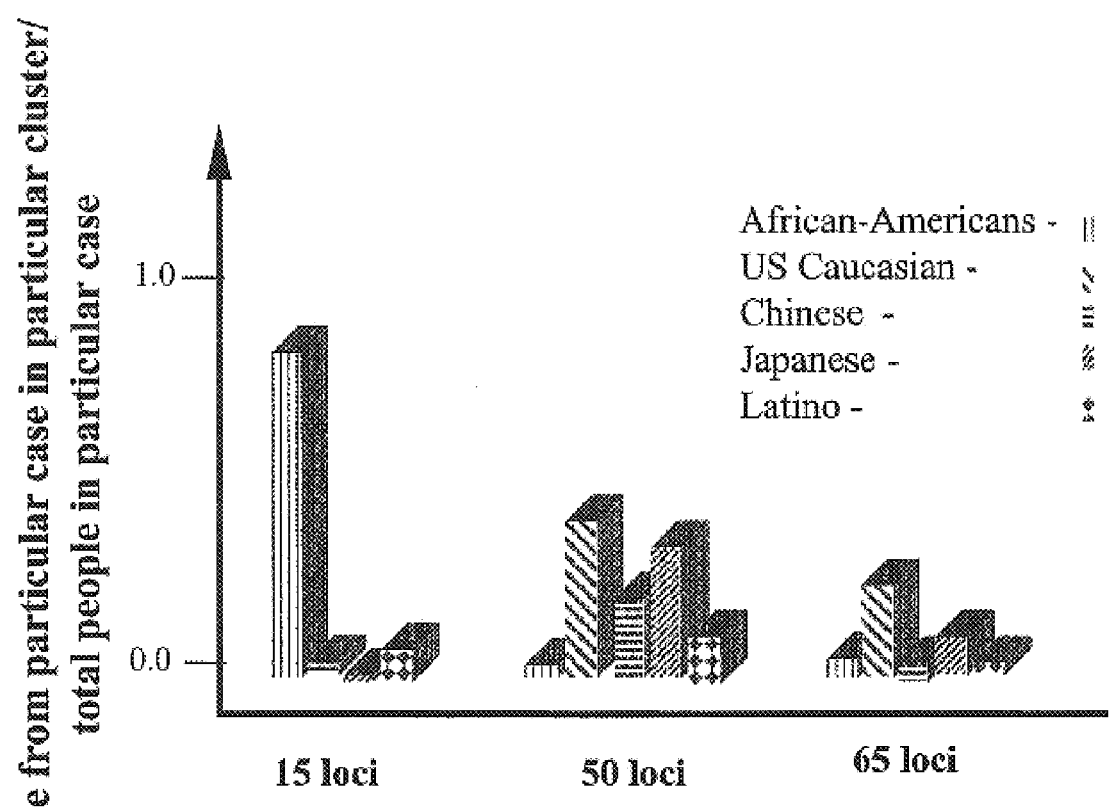
FIG. 6 shows a bar graph of the ethnic affiliation of each individual within Cluster 5 for the clustering analysis performed with 15, 50, and 65 loci.
Figure 7:
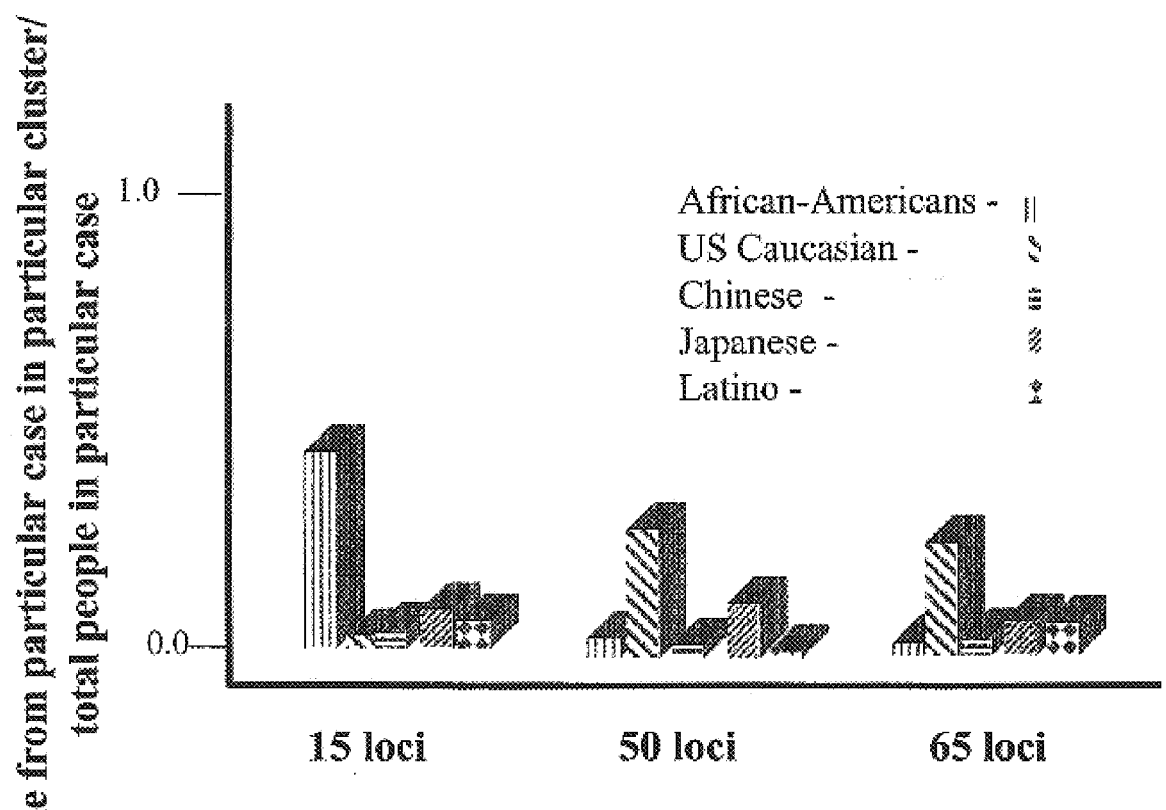
FIG. 7 shows a bar graph of the ethnic affiliation of each individual within Cluster 6 for the clustering analysis performed with 15, 50, and 65 loci.

Prior to describing the invention in more detail, the following definitions are provided for clarification.

I. Definitions

The terms "trait" and "phenotype" are used interchangeably herein and refer to any visible, detectable or otherwise measurable property of an organism such as symptoms of, or susceptibility to a disease for example.

The term "allele" is used herein to refer to variants of a nucleotide sequence. A biallelic polymorphism has two forms. Typically the first identified allele is designated as the original allele whereas other alleles are designated as alternative alleles. Diploid organisms may be homozygous or heterozygous for an allelic form.

The term "heterozygosity rate" is used herein to refer to the incidence of individuals in a population, which are heterozygous at a particular allele. In a biallelic system the heterozygosity rate is on average equal to $2P_a(1-P_a)$, where $P_a$ is the frequency of the least common allele. In order to be useful in genetic studies a genetic marker should have an adequate level of heterozygosity to allow a reasonable probability that a randomly selected person will be heterozygous.

The term "genotype" as used herein refers the identity of the alleles present in an individual or a sample. In the context of the present invention a genotype preferably refers to the description of the biallelic marker alleles present in an individual or a sample. The term "genotyping" a sample or an individual for a biallelic marker consists of determining the specific allele or the specific nucleotide carried by an individual at a biallelic marker.

The term "polymorphism" as used herein refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. A single nucleotide polymorphism is a single base pair change. Typically a single nucleotide polymorphism is the replacement of one nucleotide by another nucleotide at the polymorphic site. Deletion of a single nucleotide or insertion of a single nucleotide, also give rise to single nucleotide polymorphisms. In the context of the present invention "single nucleotide polymorphism" preferably refers to a single nucleotide substitution. Typically, between different genomes or between different individuals, the polymorphic site may be occupied by two different nucleotides.

A database includes indexed and freeform tables for storing data. Within each table are a series of fields that store data strings, such as names, addresses, chemical names, and the like. However, it should be realized that several types of databases are available. For example, a database might only include a list of data strings arranged in a column. Other databases might be relational databases wherein several two dimensional tables are linked through common fields. Embodiments of the invention are not limited to any particular type of database.

An input device can be, for example, a keyboard, rollerball, mouse, voice recognition system, automated script from another computer that generates a file, or other device capable of transmitting information from a customer to a computer. The input device can also be a touch screen associated with the display, in which case the customer responds to prompts on the display by touching the screen. The customer may enter textual information through the input device such as the keyboard or the touch-screen.

Instructions refer to computer-implemented steps for processing information in the system. Instructions can be implemented in software, firmware or hardware and include any type of programmed step undertaken by components and modules of the system.

One example of a Local Area Network may be a corporate computing network, including access to the Internet, to which computers and computing devices comprising the system are connected. In one embodiment, the LAN conforms to the Transmission Control Protocol/Internet Protocol (TCP/IP) industry standard. In alternative embodiments, the LAN may conform to other network standards, including, but not limited to, the International Standards Organization's Open Systems Interconnection, IBM's SNA, Novell's Netware, and Banyan VINES.

A microprocessor as used herein may be any conventional general purpose single- or multi-chip microprocessor such as a Pentium® processor, a Pentium® Pro processor, a 8051 processor, a MIPS® processor, a Power PC® processor, or an ALPHA® processor. In addition, the microprocessor may be any conventional special purpose microprocessor such as a digital signal processor or a graphics processor. The microprocessor typically has conventional address lines, conventional data lines, and one or more conventional control lines.

SNPs as used herein, refer to biallelic markers, which are genome-derived polynucleotides that exhibit biallelic polymorphism. As used herein, the term biallelic marker means a biallelic single nucleotide polymorphism. As used herein, the term polymorphism may include a single base substitution, insertion, or deletion. By definition, the lowest allele frequency of a biallelic polymorphism is 1% (sequence variants which show allele frequencies below 1% are called rare mutations). There are potentially more than $10^7$ biallelic markers which can easily be typed by routine automated techniques, such as sequence- or hybridization based techniques, out of which $10^6$ are sufficiently informative for mapping purposes.

The system is comprised of various modules as discussed in detail below. As can be appreciated by one of ordinary skill in the art, each of the modules comprises various sub-routines, instructions, commands, procedures, definitional statements and macros. Each of the modules are typically separately compiled and linked into a single executable program. Therefore, the following description of each of the modules is used for convenience to describe the functionality of the preferred system. Thus, the processes that are undergone by each of the modules may be arbitrarily redistributed to one of the other modules, combined together in a single module, or made available in, for example, a shareable dynamic link library.

The system may include any type of electronically connected group of computers including, for instance, the following networks: Internet, Intranet, Local Area Networks (LAN) or Wide Area Networks (WAN). In addition, the connectivity to the network may be, for example, remote modem, Ethernet (IEEE 802.3), Token Ring (IEEE 802.5), Fiber Distributed Datalink Interface (FDDI) or Asynchronous Transfer Mode (ATM). Note that computing devices may be desktop, server, portable, hand-held, set-top, or any other desired type of configuration. As used herein, an Internet includes network variations such as public internet, a private internet, a secure internet, a private network, a public network, a value-added network, an intranet, and the like.

The system may be used in connection with various operating systems such as: UNIX, Disk Operating System (DOS), OS/2, Windows 3.X, Windows 95, Windows 98, Windows 2000 and Windows NT.

The various software aspects of the system may be written in any programming language or combinations of languages such as C, C++, BASIC, Pascal, Perl, Java, and FORTRAN and ran under the well-known operating system. C, C++, BASIC, Pascal, Java, and FORTRAN are industry standard programming languages for which many commercial compilers can be used to create executable code.

A system is one or more computers and associated peripherals that carry out selected functions. For example, a Customer system includes the computer hardware, software and firmware for executing the specific software instructions described below. A system should not be interpreted as being limited to be a single computer or microprocessor, and may include a network of computers, or a computer having mutiple microprocessors.

Transmission Control Protocol (TCP) is a transport layer protocol used to provide a reliable, connection-oriented, transport layer link among computer systems. The network layer provides services to the transport layer. Using a two-way handshaking scheme, TCP provides the mechanism for establishing, maintaining, and terminating logical connections among computer systems. TCP transport layer uses IP as its network layer protocol. Additionally, TCP provides protocol ports to distinguish multiple programs executing on a single device by including the destination and source port number with each message. TCP performs functions such as transmission of byte streams, data flow definitions, data acknowledgments, lost or corrupt data re-transmissions and multiplexing multiple connections through a single network connection. Finally, TCP is responsible for encapsulating information into a datagram structure.

A programmed storage device can be any of a series of well-known programmable storage devices. Examples include, Electrically Eraseable Programmable Read Only Memories (EEPROMs) or other programmable memories known in the art. Other examples of programmed storage devices include hard disks, floppy disks, conventional memory, and the like.

2. The Invention

A basic assumption is that genetic similarity should correlate with phenotypic similarity at relevant genetic sites; there should be a relationship between genotype and phenotype. The validity of this assumption for a given population has important implications for the accuracy and the understanding of the results of a given study, for instance in studies of the genetic basis of ethnicity (Example 1) or studies to determine a genetic difference between a patient population and a control population (Example 2), among others.

A corollary to this assumption is that a given population is homogeneous; the patient and control populations for instance should be genetically different from each other in the trait studied and the loci of relevance to the determination of this trait, but should otherwise be a homogenous population. What is needed are methods to a priori determine the genetic similarity of members of a population; the number of potential clusters of genetically similar individuals or subpopulations contributing to the putative heterozygosity of a sample should be determined. If no such clusters exist, the sample is homogenous. If such clusters exist, they can and should be accounted for in an analysis of the sample.

However, up to now, the methods to determine the number of "clusters" in a population require that the number of clusters in a population is already known. Basically, given a population, one could say there should be three clusters (for example, one for Black Americans, one for Caucasians, and one for Chinese Americans), run the clustering algorithm and derive an answer. However, it was impossible to take a population containing Black Americans, Caucasians, and Chinese Americans and determine how many genetically distinct groups really existed: one, two, three, or more.

Problem to be Solved:

Approaches for cluster analysis can be classified into two types: hierarchical and non-hierarchical. In the end, the clustering method of the invention will use both hierarchical and non-hierarchical analyses. But first, a hierarchical cluster analysis is performed and used as the basis for the algorithm to determine the optimal number of clusters for the data.

Hierarchical cluster analysis produces a series of overlapping groups. The end product of a wide variety of hierarchical classification procedures is a dendrogram; these are the classical <<trees>>. This is a nested collection of clusters with two trivial extremes: the singleton and the whole set. The clusters at one level are constructed from the clusters at the previous level.

There are two basic approaches to hierarchical cluster analysis: agglomerative methods which build up clusters starting from individuals until there is only one cluster, or divisive methods which start with a single cluster and split clusters until the individual level is reached. Hierarchical cluster analysis can be represented by a tree (dendrogram) that shows at which distance the clusters merge. To every dendrogram there corresponds a unique ultrametric dissimilarity matrix.

The stages in a hierarchical analysis are usually as follows:

1. Form a distance matrix;
2. Use selected criterion to form hierarchy; and
3. Form a set of clusters and/or dendrogram.

A crucial problem in interpreting tree diagrams (hierarchical clustering) is deciding how many clusters there are from the resulting tree. If there are 100 individuals in a group, the tree diagram has all the individuals in one cluster at one end and each individual in a separate cluster (i.e. 100 clusters) at the other end. Somewhere in between is the optimum numbers of clusters for the data Typically, the researcher determines the expected number of clusters based on phenotypic data, for example, and chooses the level of the dendrogram containing this many clusters. However, no matter how the decision is made, it is relatively arbitrary, and not necessarily reflective of the underlying data.

Solution to the Problem:

Thus, to assess the inherent groups in a population a new method of the invention was necessary. Although the method of the invention was developed by comparing the pairwise similarity of alleles, it can be applied to any trait in a population to which weighted values can be assigned to determine the heterogeneity or homogeneity of the population for the trait.

Weight Function:

The first step was to identify a weight function for the sharing of alleles between members of a population.

A measure of the pairwise similarity between individuals in a sample can be defined as:

$$S_{ij} = \sum_{k=1}^{L} \frac{a_{k,ij} \cdot w_{r,k,ij} \cdot w_{h,k,ij}}{2L}$$

where i and j denote the particular individuals;

where k denotes a particular locus;

where L denotes the total number of loci;

where $a_{k,ij}$ equals 0 for locus k when individuals i and j share no common allele, $a_{k,ij}$ equals 1 for locus k when individuals i and j have one common allele, and $a_{k,ij}$ equals 2 for locus k when individuals i and j have two common alleles;

where $w_{r,k,ij}$ denotes a weight function for sharing rare alleles; and where $w_{h,k,ij}$ denotes a weight function for sharing a homozygous genotype at the locus.

The weighting will vary depending on the comparison that you are making and the desired outcome. It can be given as discrete numbers for instance 30 and 30 as used in Examples 2 and 3 herein, or it can be written as a function. For instance if you are looking specifically for individuals with a rare allele, the presence of this shared allele could be given a very high value-2,000 for example. The weighting can also be described as a function, which in this case should be dependent on the number of loci among other things. For different studies, different wieght functions would be appropriate and could be determined by those of ordinary skill in the art.

Distance Matrix:

A distance matrix can then be generated from the pairwise similarity matrix for the individuals through a number of means, one of which is the Euclidean squared distance:

$$d_{jk} = \sum_{i=1}^{k} (S_{ji} - S_{ki})^2$$

A suitable distrance matrix provides a measure of how similar individuals are to each other, in this case genetically. Common distances that are used and are appropriate for use in the methods of the invention include, but are not limited to, Euclidean distance, Euclidean squared distance, absolute distance (city block metric), and a correlation coefficient.

Hierarchical Clustering:

Subsequently, agglomerative (hierarchical) clustering methods are applied to produce a dendrogram (or tree). The tree starts with n clusters, each with a single individual, and then at each subsequent step (n-1, n-2, n-3, etc) two clusters merge to form a larger cluster until all the individuals are present in a single cluster. To determine which two clusters merge at each subsequent step, the clustering algorithm calculates the minimum variance within each cluster based on the distance between the pairwise similarity of individuals in the cluster based on the distance matrix (described above):

$$d_{i,jk} = \frac{(n_i + n_j)d_{ij} + (n_i + n_k)d_{ik} - n_i d_{jk}}{n_i + n_j + n_k}$$

where $n_i$, $n_j$, $n_k$ are the number of individuals in each cluster, i, j, k. The two clusters that when combined produce the minimum within-cluster variance, are then combined to form a single cluster, and the clustering algorithm then recalculates the minimum variance and the process continues until there is only one cluster. Alternatives to using a measurement of the minimum variance include nearest neighbor, furthest neighbor, group average, or median computations, for example, or any other method typically used in the art.

Optimal Cluster Number Determination:

The results of the hierarchical clustering algorithm are then used to determine the optimal number of clusters. The optimal number of clusters is found at the point in the tree where the average of the pairwise similarity for the individuals in the newly formed cluster (average intracluster similarity) is smaller than the average of the pairwise similarity for the individuals in either of the two parent clusters. This can also be seen as the point where the average pairwise intracluster similarity for either of two parent clusters is larger than the average pairwise intracluster similarity for a new cluster.

The following criterion is applied as an indicator for the number of clusters present in the data:

$$[\overline{S}_k]_L \leq [\overline{S}_m]_{L-1} \; \{\text{for } \forall k, \forall m\}$$

where the subscripts k and m indicate the number of clusters in step L and L-1 respectively, and $\overline{S}_k$ is the average intracluster similarity defined as:

$$\overline{S}_k = 2 \sum_{i<j=2}^{n} \frac{S_{ij}}{n(n-1)}$$

The average intracluster similarity of clusters <<k>> is compared with the average intracluster similarity of the two, parental, k-1 clusters. If either of the parental k-1 clusters have an average intracluster similarity smaller than the average intracluster similarity of the newly formed k cluster, the number of optimal clusters for the data is found at k-1.

Non-hierarchical Clustering:

Once the optimal number of clusters is determined, a non-hierarchical clustering algorithm, which requires that the number of clusters in a population be defined prior to running the algorithm, is run on the data. The non-hierarchical cluster analysis partitions the set of individuals into the pre-determined number of clusters (as determined above) so as to optimize the intracluster sum of squares (e.g. by the K-means clustering method) of the previously generated pairwise similarities from the pairwise similarity matrix. The optimal intracluster sum of squares results when the global minimum is reached.

Other classifiers that may be used for K-means clustering include, but are not limited to, nearest neighbor method (K-NNM), weighted K-NNM, and pseudo nearest neighbor combined classifier. Combinations of different classfiers can be made in order to construct more effective classification rules (Ed. S. K. Pal & P. P. Wang, *Genetic Algorithms for Pattern Recognition*, CRC Press 1996). In another alternative, a modal clustering method could be used in which not distance, but gradient, becomes of importance.

The result from non-hierarchical clustering is that the individuals in the popultion are optimally distributed into the optimal number of clusters.

Paired-pair Analysis:

Additional factors to be resolved are the potential presence of multiple <<types>> of homozygotes, heterozygotes, or both within each cluster. The similarity measure, only weights homozygosity or heterozygosity within a pair. As a result, in a comparison of two sets of paired individuals that have, for example, the same similarity score, one can have two sets of paired individuals that are homozygous or heterozygous at the same locus and two sets of paired individuals that are homozygous or heterozygous at two different loci. Similarly, one can have two sets of paired individuals that share the same homozygous or heterozygous allele, and two sets of paired individuals where the homozygous or heterozygous allele is different.

To resolve the issue of homozygosity or heterozygous, a paired-pair analysis has been developed, where the homozygous or heterozygous loci of two pairs are compared pairwise to determine whether the pairs share the same homozygous or heterozygous alleles on the same loci:

$$Z_{k,l} = \sum_{i=1}^{L} a_i$$

where $a_i=1$ when two sets of pairs have the same homozygous or heterozygous alleles on the same loci, otherwise $a_i=0$;

where L denotes the total number of loci;

where k and l each represent different pairs of individuals in a particular cluster; and where k=1, ..., N, and l=1, ..., N, where N is the number of individuals in particular cluster.

Subsequently, the average score (sum of $Z_{kl}$) of said paired-pair comparison for all pairs in a cluster is computed:

$$W_{kl} = \sum_{i>j=1}^{N} Z_{ij}$$

$$\overline{Z} = \frac{\sum_{i>j=1(ij \neq kl)}^{N} W_{ij}}{M}$$

where M is the number of permutations of paired-pairs, and $W_{kl}$ is the sum of the paired-pair comparison of one pair versus all pairs in a cluster.

Subsequently, the sum of the comparison of one pair versus all pairs in a cluster is compared with the average sum for all pairs in order to assign a value to the homozygous or heterozygous relatedness of each member of a pair to all homozygotes or heterozygous in a cluster: if, $$\overline{W}_{kl} \geq \overline{Z} \text{ then } \begin{cases} a_{i,lo} = 0 \\ a_{i,ob} = 1 \end{cases}$$
$$W_{kl} < \overline{Z} \text{ then } \begin{cases} a_{i,lo} = 1 \\ a_{i,ob} = 0 \end{cases} \text{ for each } k > 1 = 1, \ldots, N; \text{ and } i = k, 1$$

where $a_{lo}$ indicates that the individual's score for W is "below" the average score for the cluster, and where $a_{ob}$ indicates that the individual's score for W is "above" the average score for the cluster.

Next, the total number of "a"s for each individual is computed:

$$b_{k,lo} = \sum_{k>l=1}^{N} a_{k,lo} \text{ for each individual } k \text{ in particular cluster.}$$

$$b_{k,ob} = \sum_{k>l=1}^{N} a_{k,ob}$$

This allows a comparison of the number of times the sum for a pair is greater than or equal to the average sum of all pairs with the number of times the sum for a pair is less than the average sum for all pairs, for each individual in a given cluster.

The decision if and how to split a particular cluster is based on the "b" score for each individual. One cluster is constructed for individuals for which the following is satisfied:

$$b_{k,lo} \geq b_{k,ob}$$

Individuals for which this is not satisfied are assigned to another cluster. Thus, a cluster is divided into a first cluster and a second cluster if there is:

a first group of members of a cluster where the number of times the sum of one pair is less than the average sum of pairs is greater than or equal to the number of times the sum for one pair is greater than or equal to the average sum for all pairs, and a second group of members of a cluster wherein the number of times the sum of one pair is less than the average sum of pairs is less than the number of times the sum for one pair is greater than or equal to the average sum for all pairs, and where the first group of members are placed into the first cluster and the second group of members are placed into the second cluster.

Values can be assigned to the homozygous or heterozygous relatedness of each member of a pair to all homozygotes or heterozygous in said cluster based on whether the sum for one pair is greater than or equal to the average sum of all pairs, or whether the sum for one pair is less than the average sum for all pairs. The number of times the sum for one pair is greater than or equal to the average sum of all pairs with the number of times the sum for one pair is less than the average sum for all pairs for each individual in said cluster. These methods are given and described in more detail in the Detailed Description of the Invention. Equations that are superficially different but that achieve the same result are considered to be part of the claimed invention. In all cases where the paired-pair analysis is discussed, equations and analysis of homozygosity apply equally as equations and analysis of heterozygosity.

3. Implementation

Implementation of the methods of the invention in software and on computer systems is described in detail herein in the Implementation of Methods of the Invention section.

PREFERRED EMBODIMENTS OF THE INVENTION

I. Methods of Clustering Members of a Sample

The invention features methods of clustering members of a sample. Although the examples and the preferred embodiments are focussed towards genetic analysis, these methods can be used on any data needing clustering. Therefore "members" is used herein to mean the objects or individuals (or individual objects) that make up a sample. A "sample" encompass anything made up of discrete objects that can be grouped in some way. This could be as simple as a group of wooden blocks or as complex as a population of people.

Advantages of this preferred embodiment include weighting rare traits as part of the similarity calculation. This allows a more accurate determination of whether the sample is homogenous or heterogenous for the traits studied. It also permits members of great interest to be identified as a result of the rareness of a trait. Other advantages include the clustering of members of a sample without having to rely on a subjective analysis of the number of groups present by determining the "optimal number of clusters" resulting from a hierarchical clustering algorithm, and a paired-pair analysis that permits the determination of the similarity of pairs of homozygous pairs. "Homozygous" pairs can be used to refer to the sharing of the same allele genetically, or to the sharing of the same value for any trait under study.

Either as part of the method, or in preparation to perform the method, the traits to be studied must be identified. The identification of the traits is dictated by the questions asked and will vary depending on the sample. For example, to determine the overall similarity of a population, dispersed traits might be assessed; to determine whether a particular group is present in a population, traits relating to that group in particular would be assessed. The genotypes of particular loci are an example of traits. The specific loci chosen to be used in the cluster analysis for any given population will depend on the population and the question asked. For the Examples using the methods of the invention, SNPs have been used. Use of these values for traits is advantageous over RFLPs, etc, but these other forms of genetic information can also be used.

Values also have to be assigned to different aspects of a given trait. By "value" is meant a numerical representation of the desirability of a certain aspect of a trait being shared between two members of a sample. Again, this can either be done as part of the methods of the invention, or as a prior step, since the values given will relate primarily to the design of the study. However, in general, values are assigned based to some extent on the frequency or desirability of a particular aspect of a given trait. In the example provided, values are assigned based on the alleles at genetic loci. Therefore, when a pair of members share no common allele, this is valued as 0; when a pair of members share a common allele this is valued as 1; and when a pair of members share two common alleles this is valued as 2. Part of the judgement is that the study is designed to look for similarity.

In a related aspect, weights are assigned for some values based on the frequency of selected trait values in said sample. By "weights" is meant a value that can take the form of a number or a function. Weights are generally applied to trait values shared between two members of the population that are rare or are desirable (in the sense of wanting to be known/identified) or both. For example, weights can be assigned for sharing rare alleles between a pair of members, and for sharing a homozygous genotype between a pair of members. Again, the shared trait values to be weighted will differ for each study. In the present case, since similarity between pairs is desired, sharing of a homozygous genotype (sharing two of the same allele at a particular locus, e.g. "AA") was given a weight of "30". Rare alleles were also given a value of "30". Rare alleles would be those that are the less frequently observed allele of the SNP; this is determined based on empirical data. Other trait values can be weighted in similar manner according to the study design. In addition, weight functions can be drafted, in this case allowing variation of the weighting depending on the size of the population, for example.

An ordered set of similarity data is formed by the methods of the invention by determining the similarity between pairs of members of said sample using said trait values and said weights. The ordered set of similarity data can be present in a similarity matrix, but so long as the data is ordered in such a way as to permit its use in clustering algorithms it need not be in a similarity matrix. One of ordinary skill in the art would be able to determine other acceptable forms to allow the methods of the invention. The similarity data set or similarity matrix can be formed based on the pairwise similarity measure:

$$S_{ij} = \sum_{k=1}^{L} \frac{a_{k,ij} \cdot w_{r,k,ij} \cdot w_{h,k,ij}}{2L}$$

where i and j denote the particular members;
where k denotes a particular locus;
where L denotes the total number of loci;
where $a_{k,ij}$ equals 0 for locus k when members i and j share no common allele,
  $a_{k,ij}$ equals 1 for locus k when members i and j have one common allele, and
  $a_{k,ij}$ equals 2 for locus k when members i and j have two common alleles; where
$w_{r,k,ij}$ denotes a weight function for sharing rare alleles; and
where $w_{h,k,ij}$ denotes a weight function for sharing a homozygous genotype. Other pairwise similarity measures can also be used so long as they permit (or can be modified to permit) the incorporation of the weight functions.

An ordered set of distance data can be calculated from the ordered set of similarity data. Alternatively, the ordered set of distance data can be calculated from the similarity matrix. Alternatively, the distance data is present in a distance matrix. The distance matrix can be generated using distances selected from the group consisting of Euclidean squared distance, Euclidean distance, absolute distance, and correlation coefficient. Most preferably, the distance matrix is generated using Euclidean squared distance. However, one with skill in the art would be able to determine other distance measurements that can be used for this comparison. Any distance measurement that can be used in hierarchical clustering is specifically contemplated for use. An exemplary distance algorithm is given in the Detailed Description of the Invention.

A hierarchical clustering algorithm is then applied to the ordered distance data or distance matrix. The hierarchical clustering algorithm produces a dendrogram based on calculations selected from the group consisting of minimum variance, nearest neighbor, furthest neighbor, group average, and median computations. Preferably, the hierarchical clustering algorithm produces a dendrogram based on minimum variance calculations. However, one with skill in the art would be able to determine other bases for the hierarchical clustering algorithm. Any base that permits hierarchical clustering is specifically contemplated for use. An exemplary hierarchical clustering algorithm is given in the Detailed Description of the Invention.

The optimal number of clusters can be determined based on the results of the hierarchical clustering algorithm. By "optimal number of clusters" is meant the number of distinct groups in a sample where to add one more cluster would mean that the overall level of similarity within each cluster would decrease rather than increase. The optimal number of clusters is found where the average pairwise intracluster similarity for two parent clusters is larger than the average pairwise intracluster similarity for a new cluster. An algorithm representing this is provided in the Detailed Description of the Invention. Other algorithms that achieve the same result by different means are considered to also be part of the claimed invention.

A non-hierarchical clustering algorithm can be applied to the ordered set of similarity data (or the similarity matrix) using the optimal number of clusters. Any non-hierarchical clustering algorithm known in the art can be used, although preferably the non-hierarchical clustering algorithm uses K-means clustering. Preferably, the K-means clustering uses classifiers selected from the group consisting of sum of squares, nearest neighbor method, weighted nearest neighbor method, and pseudo nearest neighbor combined classifier, although others in the art are also specifically envisioned to be used. Most preferably, said classifier is sum of squares.

The relatedness between pairs of homozygous pairs can be determined by performing a paired-pair analysis on the clusters resulting from the non-hierarchical clustering algorithm, where the homozygous loci of two pairs are compared pairwise to determine whether the pairs share the same homozygous alleles on the same loci. Equations detailing this and the following steps are provided in the Detailed Description of the Invention. Equations that are different but that achieve the same result are considered to be part of the claimed invention. In addition, alternative computer embodiments are described under Implementation of the Methods of the Invention, herein.

A cluster is then divided into a first cluster and a second cluster if there is: a first group of members of said cluster wherein said number of times said sum of one pair is less than said average sum of pairs is greater than or equal to said number of times said sum for one pair is greater than or equal to said average sum for all pairs, and a second group of members of said cluster wherein said number of times said sum of one pair is less than said average sum of pairs is less than said number of times said sum for one pair is greater than or equal to said average sum for all pairs, and wherein said first group of members are placed into said first cluster and said second group of members are placed into said second cluster. This step can optionally be repeated if there is a question whether the resulting cluster(s) contains more than one group of homozygous members.

II. Methods of Non-hierarchical Clustering

The invention also features methods of non-hierarchical clustering of members of a sample that includes using paired-pair analysis to distinguish among the various homozygous forms that may be present in a sample, and determine whether in fact the clusters should be further separated. This step can be repeated as necessary.

A non-hierarchical clustering algorithm is applied to a sample, either as part of the method, or as a prior step; alternatively a sample that is thought to be a population, but that has homozygous members, can be assessed by this method, whether or not a non-hierarchical clustering method is performed on it. Thus, this method can be used on any population to assess the presence of more than one group of homozygous members.

The relatedness between pairs of homozygous pairs is determined by performing a paired-pair analysis on the clusters resulting from said non-hierarchical clustering algorithm using the same methods that are described in the first Preferred Embodiment of the Invention and the equations discussed in the Detailed Description of the Invention. As stated previously, the equations set forth herein and used to achieve the desired results are exemplary and do not limit the invention to achieving the described results through the use of these equations. Other equations that achieve the same results are expressly intended to form part of the invention.

III. Methods of Detecting the Presence of Clusters in a Sample

The invention also features methods of determining the presence of clusters in a sample. This method can be used to simply determine whether for given traits a sample is homogenous. Similarly, it can be used to determine whether an individual, individuals, small group, or other population, is part of the population or whether it forms a separate group.

As described in the first Preferred Embodiment of the invention, traits are chosen, values are given, and weights are assigned based on factors determined to be relevant to the population studied and to the question asked. Similarly, an ordered set of similarity data or similarity matrix is obtained as described previously in the first Preferred Embodiment of the invention and in the Detailed Description of the Invention.

In some cases, this method further comprises calculating an ordered set of distance data or a distance matrix from said ordered set of similarity data or similarity matrix, again as described previously in the first Preferred Embodiment of the invention and in the Detailed Description of the Invention. This is useful when a hierarchical clustering algorithm is to be applied to the data.

A clustering algorithm, either hierarchical or non-hierarchical, is then applied to the ordered set of similarity data or the similarity matrix (or the ordered set of distance data or distance matrix). Hierarchical and non-hierarchical clustering algorithms have been described previously in the first Preferred Embodiment of the invention and in the Detailed Description of the Invention. If a hierarchical clustering algorithm is used, the method of determining the optimal number of clusters in a sample is preferentially used as described previously in the first Preferred Embodiment of the invention and in the Detailed Description of the Invention. The method is also described further in the fourth Preferred Embodiment of the Invention, below.

IV. Methods of Determining the Number of Clusters in a Sample

The invention also features methods of determining the number of clusters in a sample based on the results of a hierarchical clustering algorithm. Since a hierarchical clustering algorithm results in a tree with one end being the entire sample and the other end being where each member of a sample is in its own cluster, another method is necessary to determine at which point the optimal number of clusters is present. The method of the invention can be used on any set of data following its analysis by hierarchical clustering. The method of optimal clustering has been described previously as part of the first Preferred Embodiment of the invention and in the Detailed Description of the Invention.

V. Implementation of Methods of the Invention

The automated system for clustering can be implemented through a variety of combinations of computer hardware and software. In one implementation, the computer hardware is a high-speed multiprocessor computer running a well-known operating system, such as UNIX. The computer should preferably be able to calculated millions, tens of millions, billions or more floating-point operations by second. The amount of speed is advantageous for determining the homogeneity and/or heterogeneity of a population or sub-population for even the largest population sizes within a reasonable period of time. Such computers are manufactured by companies such as Intel; International Business Machines; Silicon Graphics, Incorporated; Hitachi; and Cray, Incorporated.

While it is envisioned that currently available personal computers using single or multiple microprocessors might also function within the parameters of the present invention, especially for small populations, such a computer system might be too slow to perform all the combinations of the paired-pair analysis required for large populations. However, as the efficiency and speed of micro-processor based computer systems increases, the likelihood that a conventional personal computer would be useful for the present invention also increases.

Preferably, the software that runs the calculations for the present invention is written in a language that is designed to run within the UNIX operating system. The software language can be, for example, FORTRAN, C, C++, PERL, Python, Pascal, Cobol, Java, any other computer language known, or combinations of languages. It should be noted that the nucleic acid sequence data will be stored in a database and accessed by the software of the present invention. These programming languages are commercially available from a variety of companies such as Microsoft, Compaq, and Borland International.

In addition, the software described herein can be stored on several different types of media. For example, the software can be stored on floppy disks, hard disks, CD-ROMs, Electrically Erasable Programmable Read-Only Memory, Random Access Memory, or any other type of programmed storage media.

Figure 18:
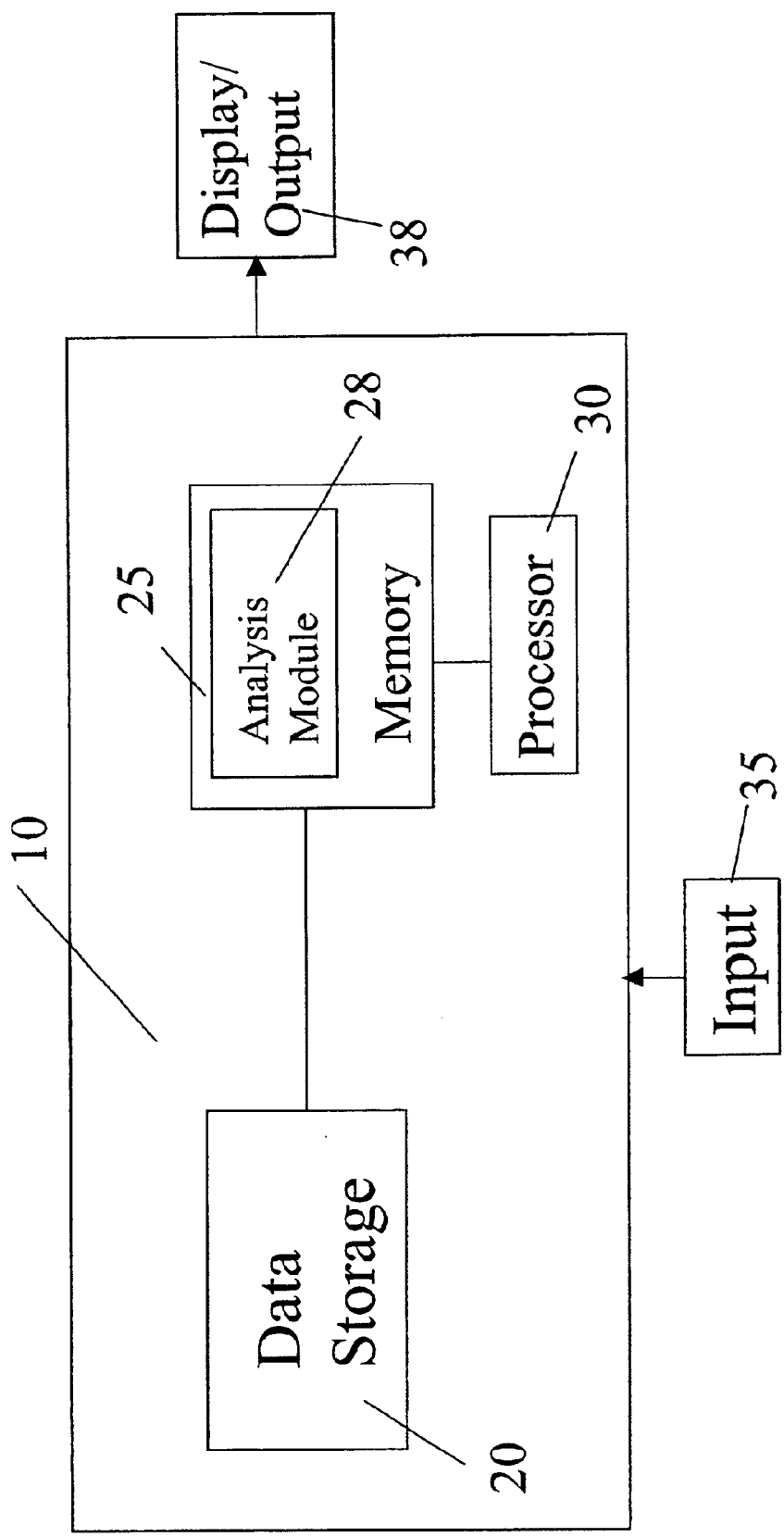
FIG. 18 shows a diagram of an automated system.

Referring to FIG. 18, a system 10 that includes a data storage 20, such as that described above, is linked to a memory 25. Associated with the memory 25 is an analysis module 28 that provides commands and instructions for the data analysis functions described below. Communicating with the memory 25 is a processor 30 that is used to process the information being analyzed within the module 28. Conventional processors, such as those made by Intel, Compaq, and Motorola are anticipated to function within the scope of the present invention. As illustrated, an input 35 provides data to the system 10. The input 35 can be a keyboard, mouse, data link, or any other mechanism known in the art for providing data to a computer system. In addition, a display 38 is provided to display the output of the analysis undertaken by the analysis module 28.

Figure 19:
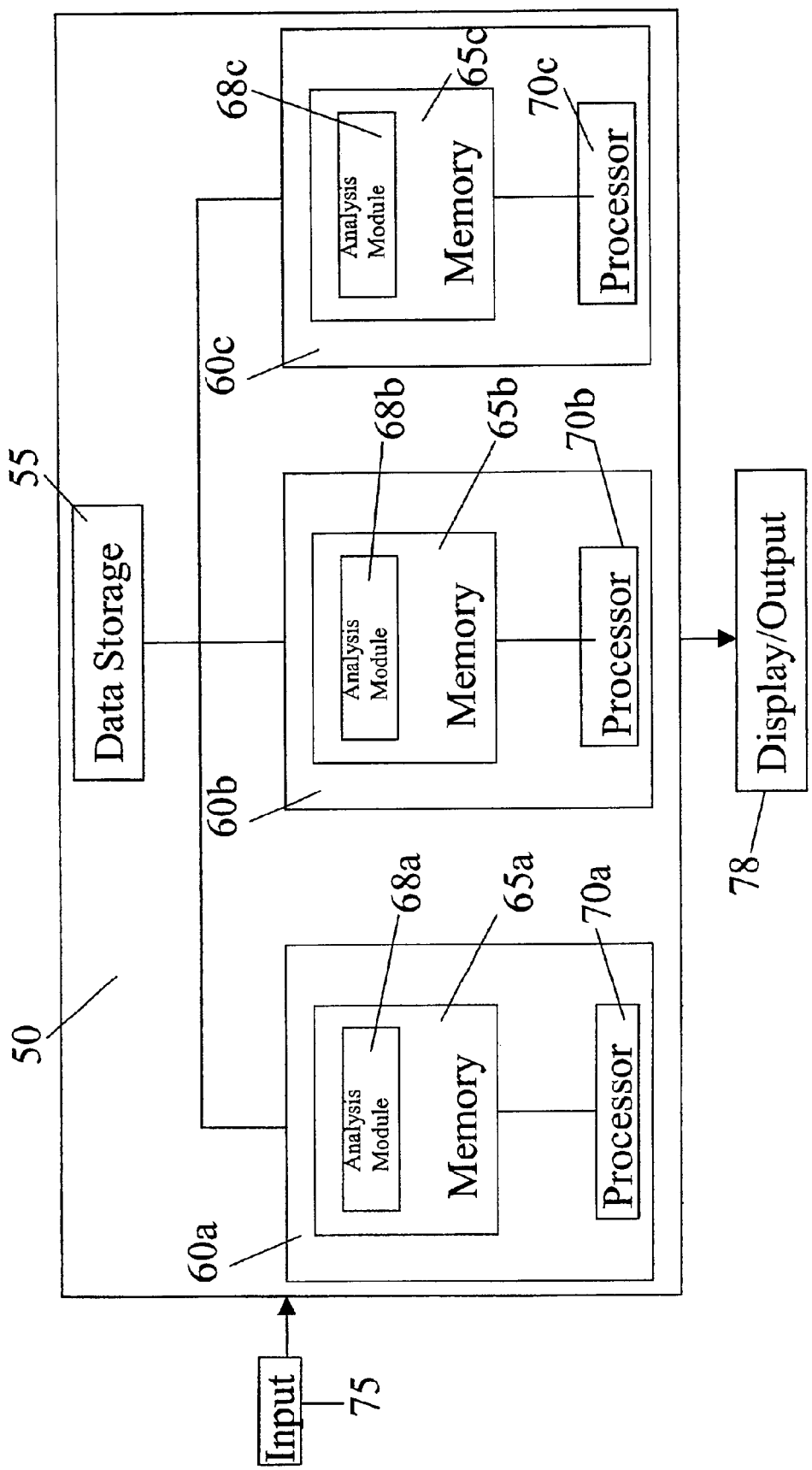
FIG. 19 shows a diagram of an alternative automated system.

Referring now to FIG. 19, an alternative system 50 that includes a data storage 55, such as that described above, but that is shared among sub-systems 60a, 60b, and 60c and is linked to memories 65a, 65b, and 65c in each sub-system. Associated with each of the memories 65a, 65b, and 65c are analysis modules 68a, 68b, and 68c that store commands and instructions for performing the data analysis functions described below. Communicating with each of the memories 65a, 65b, and 65c are processors 70a, 70b, and 70c that are used to process the information being analyzed within the analysis modules 68a, 68b, and 68c. Note that although three sub-systems are depicted in FIG. 19, their numbers can be increased or decreased as needed. Conventional processors, such as those made by Intel, Compaq, and Motorola are anticipated to function within the scope of the present invention. As illustrated, an input 75 provides data to the system 50. The input 75 can be a keyboard, mouse, data link, or any other mechanism known in the art for providing data to a computer system. In addition, a display 78 is provided to display the output of the analysis undertaken by the analysis modules 68a, 68b, and 68c for the sub-systems 60a, 60b, and 60c.

The sub-systems 60a, 60b, and 60c may be linked to the data storage 55 and to each other in a variety of ways including, but not limited to, data links or network links. Various software products may be used to facilitate the linking between sub-systems 60a, 60b, and 60c such as the publicly available Parallel Virtual Machine (PVM) and the Message Passing Interface (MPI). PVM and MPI may be obtained from http://www.epm.ornl.gov/pvm/ and http://www-unix.mcs.anl.gov/mpi/index.html, respectively.

Figure 20:
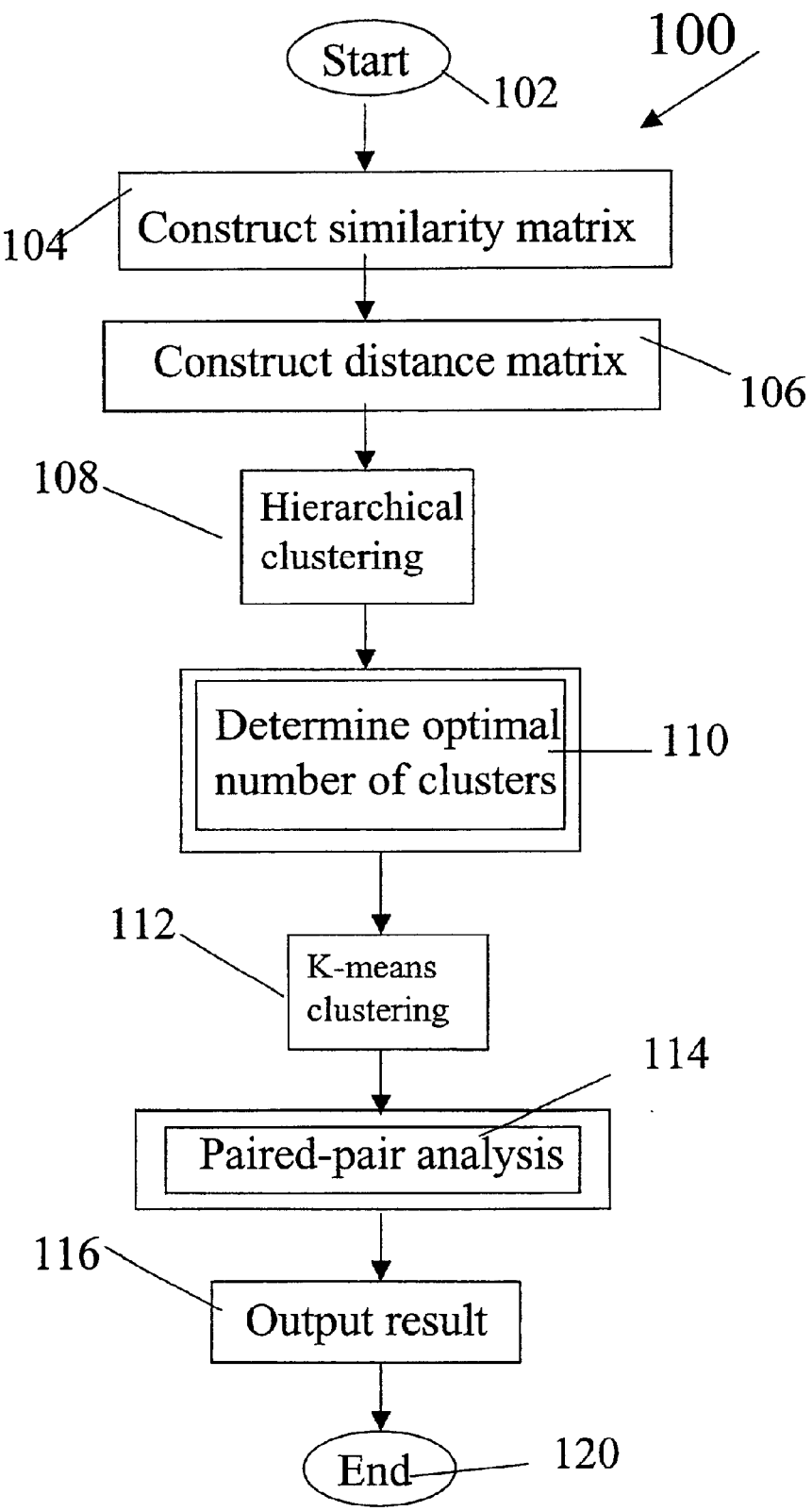
FIG. 20 shows a diagram of the process of clustering members of a population.

Referring to FIG. 20, a process 100 of genetic cluster analysis of a population is illustrated. The process 100 begins at start state 102, and then moves to a process state 104 wherein a similarity matrix is constructed. The process 100 then moves to a process state 106 wherein a distance matrix is constructed. The process 100 then moves to process state 108 wherein hierarchal clustering is performed. The process 100 then moves to process state 110 wherein the optimal number of clusters is determined based on the result of the process of 108. The process 110 of determining the optimal number of clusters is described in more detail in FIG. 21.

The process 100 then moves on to process state 112 wherein a non-heirarchal K-means clustering is used to distribute members of the population into the number of clusters identified in state 110. The process 100 then moves on to process state 114, wherein paired-pair analysis is used to determine if any of the clusters need to be divided again. Process 114 is described in more detail in FIG. 22 and in an alternative form in FIG. 23. The process 100 then moves to a state 116 wherein the result is output to a display. The process 100 then terminates at an end state 120.

Figure 21:
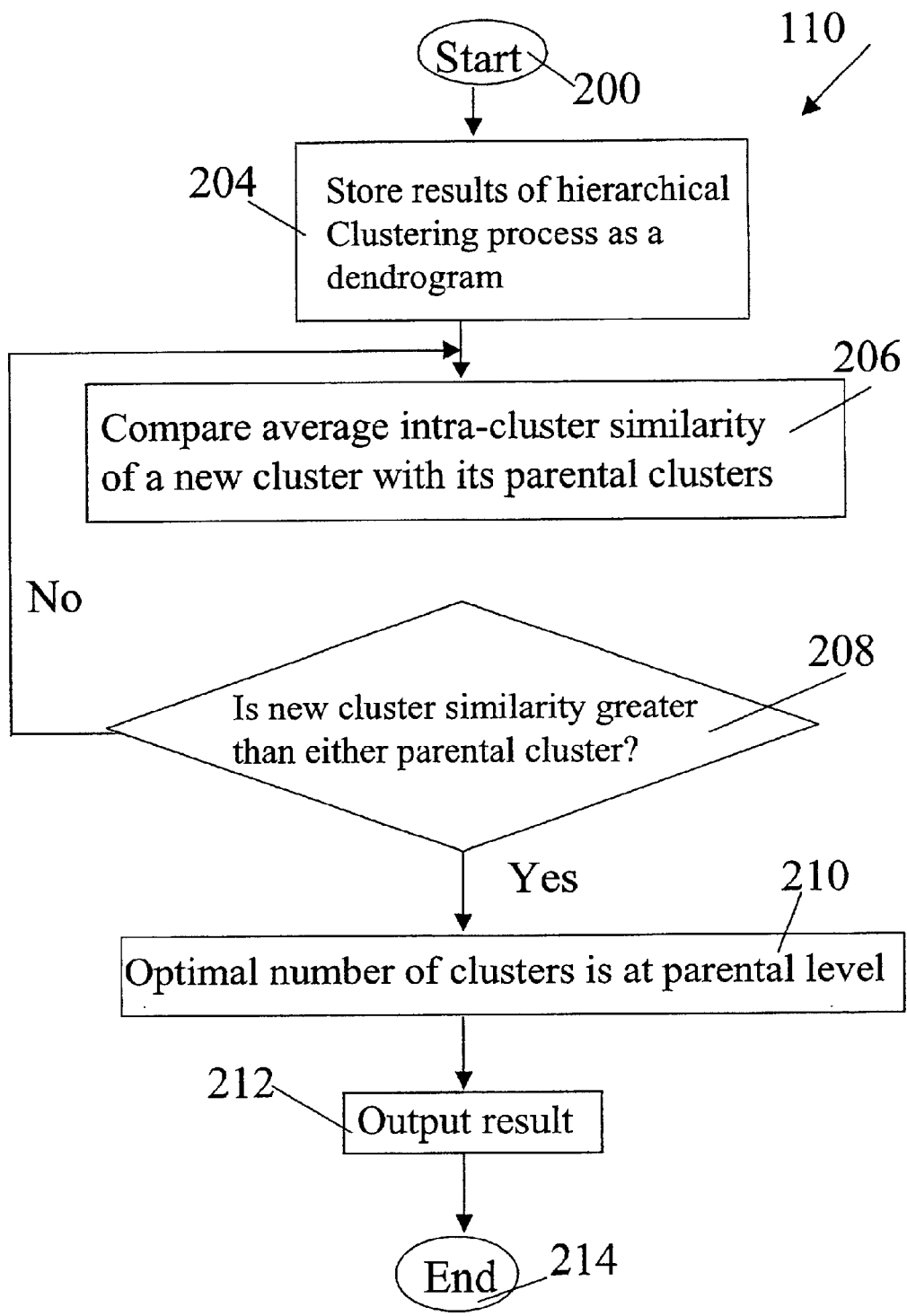
FIG. 21 shows a diagram of the process of determining the optimal number of clusters in a sample.

Referring now to FIG. 21, the process 110 of determining the optimal number of clusters in a population is illustrated. The process 110 begins at a start state 200 and then moves to a state 204 where the results of a hierarchical clustering process are stored as a dendrogram. Process 110 then moves on to a process state 206 where the average pairwise intracluster similarity of a new cluster is compared with the average pairwise intracluster similarity of its parental clusters. A determination is then made at a decision state 208 whether the average intracluster pairwise similarity of the new cluster is greater than the average intracluster pairwise similarity of either parental cluster. If the average intracluster pairwise similarity of the new cluster is not greater than either parental cluster, the process 110 returns to the 206 to compare the average intracluster pairwise similarity of the next new cluster with its parental clusters.

However, if the average intracluster pairwise similarity of the new cluster is greater than either parental cluster, the process 110 moves to a state 210 to identify the optimal number of clusters at the parental level. The process 110 then moves to a state 212 where the result is output to a display. The process 110 then terminates at an end state 214.

Figure 22:
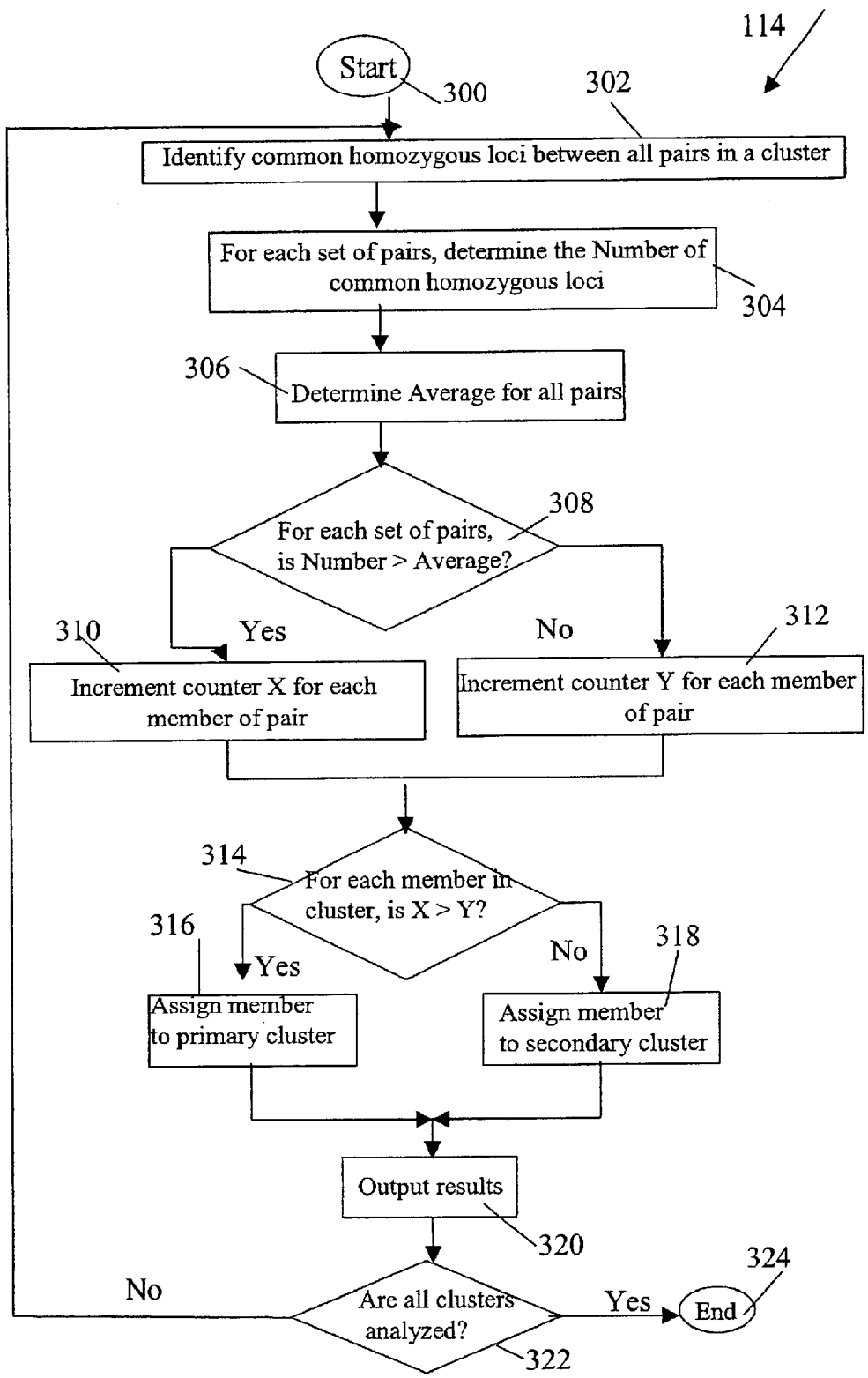
FIG. 22 shows a diagram of the process of paired-pair analysis.

Referring now to FIG. 22, one embodiment of a process 114 of paired-pair analysis is illustrated. The process 114 begins at start state 300 and then moves to a process state 302 wherein the common homozygous loci between all pairs in the similarity matrix generated at the state 104 are identified. Process 114 then moves to process state 304 wherein a paired-pair comparison is performed, such that the number of common homozygous loci between each set of pairs is determined. Process 114 then moves to process state 306 wherein the average paired-pair score for all pairs is calculated. A determination is then made at a decision state 308 for each set of pairs of whether the number of homozygous loci between a set of pairs is greater than the average score for all pairs. If the Number is greater than the Average, process 114 moves to state 310 wherein a counter X is incremented for each member of the pair. If the Number is less than the Average, process 114 moves to state 312 wherein a counter Y is incremented for each member of the pair. From state 310 or state 312, process 114 then moves to decision state 314, wherein a determination is made for each member of the cluster as to whether counter X is greater than counter Y. If X is greater than Y, process 114 moves to state 316 wherein the member is assigned to one cluster. If X is less than Y, process 114 moves to state 318 wherein the member is assigned to a second cluster. From either state 316 or 318, process 114 moves to a state 320 wherein the result is output to a display. Process 114 then moves to a decision state 322 wherein a determination is made whether all clusters have been analyzed. If all clusters have not been analyzed, the process 114 returns to state 302 to identify common homozygous loci between all pairs in a new cluster. If all clusters have been analyzed, process 114 then terminates at an end state 324.

Due to memory and clock-speed constraints imposed by the computational hardware the paired-pair analysis process described above and diagrammed in FIG. 22 may be performed over multiple computers or processors. Paired-pair analysis may be cumbersome to perform depending on the size of the population, since the number of unique pairs is determined by $(N^2-N)/2$. As a result, the number of paired-pair comparisons increases dramatically with increasing numbers of individuals in the population. For illustration purposes, if the number of members N is equal to 100, the number of unique pairs would be 4950. Then for the paired-pair analysis, where homozygous loci of pairs of individuals within a given cluster are to be compared pair-wise, 12,248,775 (($4950^2-49050$)/2) comparisons would be required to be performed. To increase the speed of the calculations as well as to remove hardware constraints such memory limitations imposed by a single computer or processor, a preferred embodiment would consist of, but not be limited to, performing the comparisons over many computers or processors, optionally at least 5.

Throughout this application, various publications, patents, and published patent applications are cited. The disclosures of the publications, patents, and published patent specifications referenced in this application are hereby incorporated by reference into the present disclosure to more fully describe the state of the art to which this invention pertains.

EXAMPLES

Several of the methods of the present invention are described in the following examples, which are offered by way of illustration and not by way of limitation. Many other modifications and variations of the invention as herein set forth can be made without departing from the spirit and scope thereof

Example 1

Use of the Genetic Clustering Algorithm to Assess the Ethnic Diversity of a Population Sample Population:

Individuals were recruited from the greater San Diego metropolitan area. Respondents were categorized into 5 major ethnic groups based upon self-reporting of the ethnic origin of both parents and all grandparents. Five ethnic classifications were chosen: African American, US Caucasian, Chinese, Japanese and Hispanic/Latino. 95 DNA samples were selected from each classification and included only samples with grandparents reported from the same classification.

All participating individuals signed informed consent agreements in this IRB approved study. Individuals were given coded identification and names were not included in the database. DNA was isolated from whole blood using standard techniques. Samples were stored frozen with bar coded labels.

Sixty-five SNPs were genotyped in each sample. Thirty-one SNPs were from a 450 kb region of chromosome 8, 19 were from an 80 kb region of chromosome 1, and 15 were unlinked SNPs randomly distributed throughout the genome. These later SNPs were expected to be significantly polymorphic (Heterozygosity>0.2) based upon a pilot SNP survey of French Caucasians in which pooled DNA samples were sequenced. SNPs used in this study, as well as the microsequencing primers, are detailed in the Sequence Listing.

SNP Detection and Mapping:

BAC libraries were obtained as described by Woo et al (*Nucleic Acids Res.* 22:4922–4931, 1994). Briefly, three different human genomic libraries were produced by cloning partially digested DNA (BamHI, HindIII or NdeI partial digests) from a human lymphoblastoid cell line (derived from individual No8445 from CEPH) into pBeloBAC11 (Kim et al., *Genomics* 34:213–218, 1996). The combined BAC library contains clones with an average insert size of 150 kb corresponding to 12 human genome equivalents. BAC clones covering the genomic region under study (around markers D8S277 and D1S2785) were obtained by screening the BAC libraries with public STSs WI-14718, WI-3831, D8S1413E, WI-8327, WI-3823 and ND4, using three-dimensional pooling (Chumakov, et al, *Nature* 377:175–297, 1995). Subchromosomal localization of the BACs selected by STS screening was verified by fluorescence in situ hybridization (FISH), performed on metaphasic chromosomes (Cherif et al, *Proc Natl Acad Sci USA* 87:6639–6643, 1990). BAC insert size was determined by Pulsed Field Gel Electrophoresis after digestion with NotI. The BACs selected by STS screening and verified by FISH, were assembled into contigs and new markers were generated by partial sequencing of insert ends from some of them.

BACs were individually subcloned in pBluescript II Sk (+) vector following standard procedures and were obtained by sequencing of these plasmid subclones. An average of 500 bases at each end of the subclone was determined by fluorescent automated sequencing on ABI 377 sequencers (Perkin Elmer), using a dye-primer cycle sequencing protocol and ThermoSequenase (Amersham Life Science).

The sequence fragments from the BAC subclones were assembled using Gap4 software from R. Staden (Bonfield, et al, *Nulceic Acids Res.* 23:4992–4999, 1995). Where required, directed sequencing techniques (primer walking) were used to complete sequences and link contigs. Unique contigs representing the consensus sequence were finally reconstructed from the alignment of different fragments. The consensus sequence was first analyzed using an automated software which eliminates repeat sequences.

To identify common SNPs, primer pairs were derived from consensus sequence using the OSP software (Hillier and Green, *PCR Methods Appl.* 1: 124–8, 1991). Amplicons investigated covered both potential exons and random genomic regions. The PCR primers were then used to amplify the corresponding genomic sequences in a pool of DNA from 100 unrelated individuals (blood donors of French origin). PCR reactions (25 mL total volume) contained 2 ng/$\mu$L pooled DNA, 2 mM $MgCl_2$, 200 $\mu$M each dNTP, 2.9 ng/µL each primer, 0.05 unit/µL Ampli Taq Gold DNA polymerase (Perkin Elmer) and 1×PCR buffer (10 mM TrisHCl pH 8.3, 50 mM KCl). Amplification reactions were performed in a PTC200 MJ Research thermocycler, with initial denaturation at 95° C. for 10 min followed by 40 cycles of denaturation at 95° C. for 30 sec, annealing at 54° C. for 1 min, and extension at 72° C. for 30 sec. After cycling, a final elongation step was performed at 72° C. for 10 min. Amplification products from pooled DNA samples were sequenced on both strands by fluorescent automated sequencing on ABI 377 sequences (Perkin Elmer), using a dye-primer cycle sequencing protocol and ThermoSequenase (Amersham Life Science). Following gel image analysis and DNA sequence extraction with ABI Prism DNA Sequencing Analysis software, sequence data were automatically processed with AnaPolys (Genset), a software designed to detect the presence of SNPs among pooled amplified fragments. The polymorphism search is based on the presence of superimposed peaks in the electrophoresis pattern from both strands, resulting from two bases occurring at the same position. The detection limit for the frequency of SNPs detected by sequencing pools of 100 individuals is about 10% for the minor allele, as verified by sequencing pools of known allelic frequencies. However, more than 90% of the SNPs detected by the pooling method have a frequency for the minor allele higher than 20%.

Genotyping:

Heterozygote scoring for the six combinations of A, C, G, T were reported by our software as AC, AG, AT, CG, CT or GT. Therefore, we designated the first allele as allele1 and the second as allele2 for all disequilibrium calculations. Genotyping of individual DNA samples was performed using a microsequencing procedure as follows. Amplification products containing the SNPs were obtained by performing PCR reactions similar to those described for SNP identification. After purification of the amplification products, the microsequencing reaction mixture was prepared by adding in a 20 µL final volume: 10 pmol microsequencing primer (which hybridizes just upstream of the polymorphic base), 1 U of Thermosequenase (Amersham) or TaqFS (Perkin Elmer), 1.25 µL Thermosequenase buffer (260 mM Tris HCl pH 9.5, 65 mM $MgCl_2$) or 2.5 µL 5×CSA Sequencing Buffer (Perkin Elmer), and the two appropriate fluorescent ddNTPs (Perkin Elmer, Dye Terminator Set) complementary to the nucleotides at the polymorphic site of each SNP tested. After 4 minutes at 94° C., 20 microsequencing cycles of 15 sec at 55° C., 5 sec at 72° C., and 10 sec at 94° C. were carried out in a GeneAmp PCR System 9700 (PE Applied Biosytems). After reaction, the 3'-extended primers were precipitated to remove the unincorporated fluorescent ddNTPs and analyzed by electrophoresis on ABI 377 sequencers. Following gel analysis with GENESCAN software (Perkin Elmer), data were automatically processed with AnaMIS (Genset), a software that allows the determination of the alleles of SNPs present in each amplified fragment based on fluorescent intensity ratios.

SNP Data Analysis:

Genotype data was compiled and checked for scoring accuracy with 32 duplicated samples. Sporatic PCR failures were tolerated as long as the number of genotypes for any one SNP in any one ethnic group did not fall below 88. The SNPs used for this study are provided in the Sequence Listing.

Genetic Cluster Analysis of the Total Population:

Cluster analysis, using the genetic clustering algorithm of the invention (Detailed Description of the Invention), was performed on the total population of 475 individuals (all ethnic groups combined). Cluster analysis was performed using three different sets of SNP genotype results: 1) using 15 loci randomly distributed throughout the genome, 2) using 50 loci distributed over chromosome 1 and 8, and 3) using all 65 loci together (FIG. 1). If the genetic diversity of the individuals matched their claimed ethnic diversity, we should have 5 clusters for each set of loci. In contrast, the results show that when 65 loci are used, 9 clusters arc found, and when 15 or 50 loci are used, six clusters are formed In fact, the number of groups found is relatively SNP-dependent, since different numbers of clusters are found with different sets of SNPs and the composition of the clusters is different for the different sets of SNPs. This indicates the importance of the choice of loci to use for genetic clustering analysis.

Figure 8:
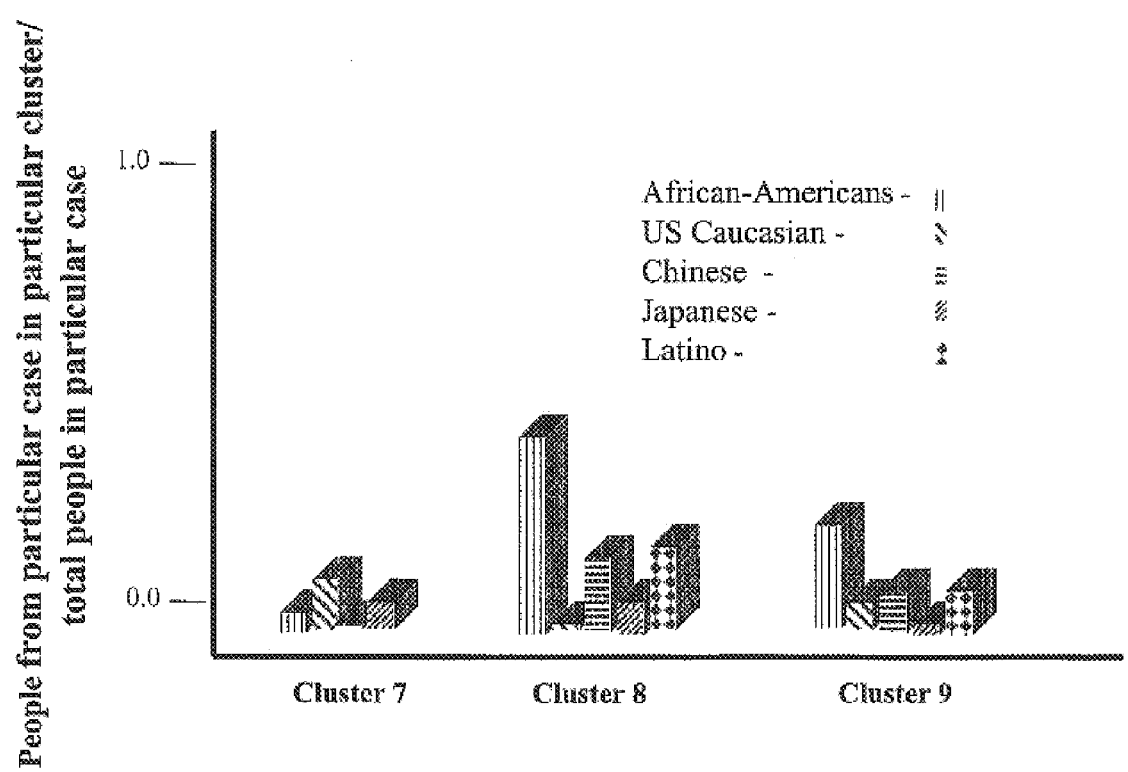
FIG. 8 shows a bar graph of the ethnic affiliation of each individual within Cluster 7, Cluster 8, and Cluster 9 for the clustering analysis performed with 65 loci.

Subsequently, the individuals in each cluster for each analysis (with 15, 50 or 65 loci) were identified based on their reported ethnic identity (FIGS. 2–8). Again, if the genetic diversity of the individuals for these loci is related to their ethnic diversity, we should see predominantly one ethnic group in each cluster. However, members of the different ethnic groups are found across all clusters (although in differing ratios) based on results from any of the 3 groups of loci with four exceptions: 1) no Chinese individuals were found in Cluster 2 when 65 loci were used for analysis (FIG. 3), 2) no African Americans were found in Cluster 4 when 15 loci were used for analysis (FIG. 5), 3) no US Caucasians were found in Cluster 5 when 15 loci were used for analysis (FIG. 6), and 4) no African Americans were found in Cluster 7 when 65 loci were used for analysis (FIG. 8).

An examination of the clusters resulting from the analyses shows that to some extent the African American group can be separated from the other ethnic groups. The analysis using 15 loci shows that there are: two clusters, Cluster 5 and Cluster 6 (FIGS. 6 and 7, respectively), that contain predominantly African American individuals; three clusters, Cluster 1, Cluster 2, and Cluster 3 (FIGS. 2, 3, and 4, respectively), that contain predominantly non-African American individuals; and one cluster, Cluster 4 (FIG. 5), that contains about equal numbers of individuals from all the ethnic groups. The analysis using 50 loci shows that there are: one cluster, Cluster 1 (FIG. 2), that contains predominantly African American individuals; and three clusters, Cluster 3, Cluster 5, and Cluster 6 (FIGS. 4, 6, and 7, respectively), that contain predominantly non-African American individuals. When all 65 loci are used, the separation among the clusters is less clear, although two clusters, Cluster 8 and Cluster 9 (FIG. 8), and to some extent Cluster 1 (FIG. 2), show predominantly African American individuals, while two clusters, Cluster 3 and Cluster 4 (FIGS. 4 and 5, respectively), show predominantly non-African Americans.

Thus, this analysis indicates that it is likely that loci can be identified that would be able to differentiate between at least African American and other ethnic groups. Potentially, using different loci or subgroups of loci, it may be possible to also differentiate among the other ethnic groups.

Figure 9:
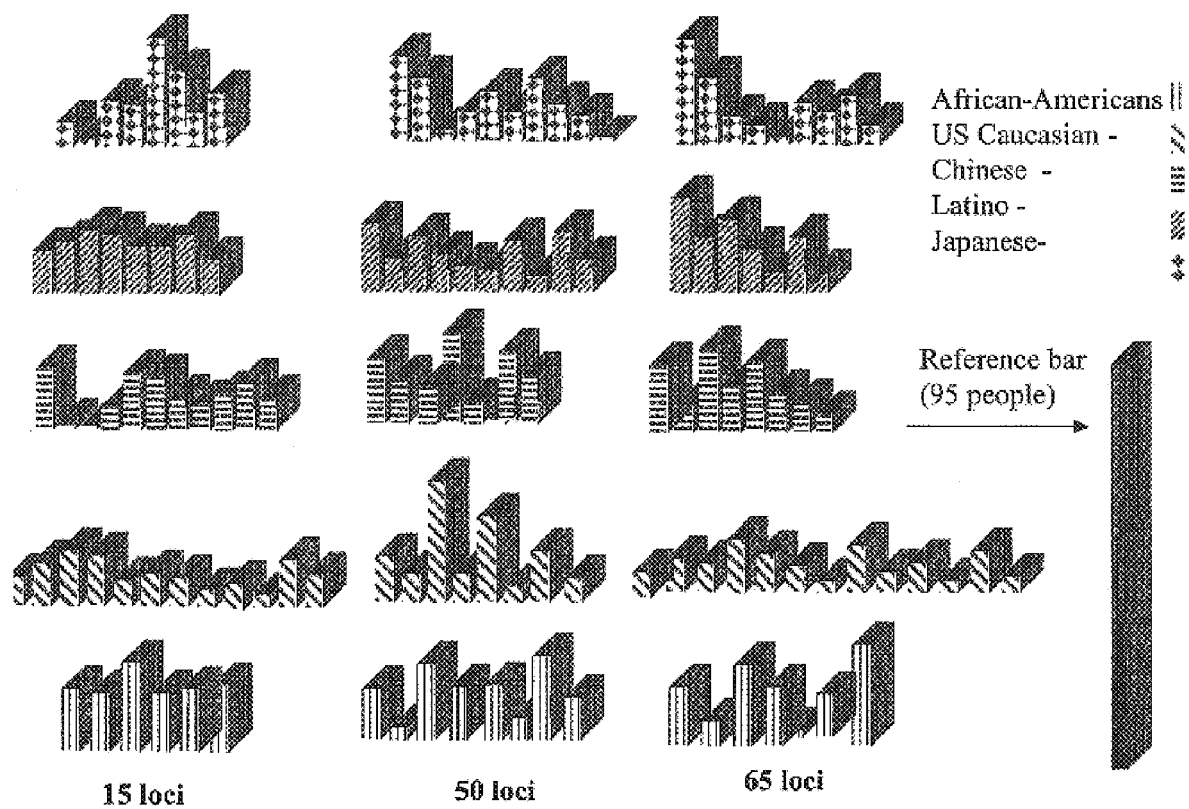
FIG. 9 shows a graphical representation of the results of the clustering analysis performed separately on each ethnic group using 15, 50, and 65 loci.

Genetic Cluster Analysis of Each Ethnic Population:

Cluster analysis, using the genetic clustering algorithm of the invention (Detailed Description of the Invention), was performed on each ethnic group separately, using the SNP genotype results from the 15, 50, and 65 loci (FIG. 9). If each ethnic group was genetically similar for the loci studied, then only one cluster should be present. However, the data show that within each ethnic group there are many genetic clusters. This is especially striking for the US Caucasian group.

Figure 10:
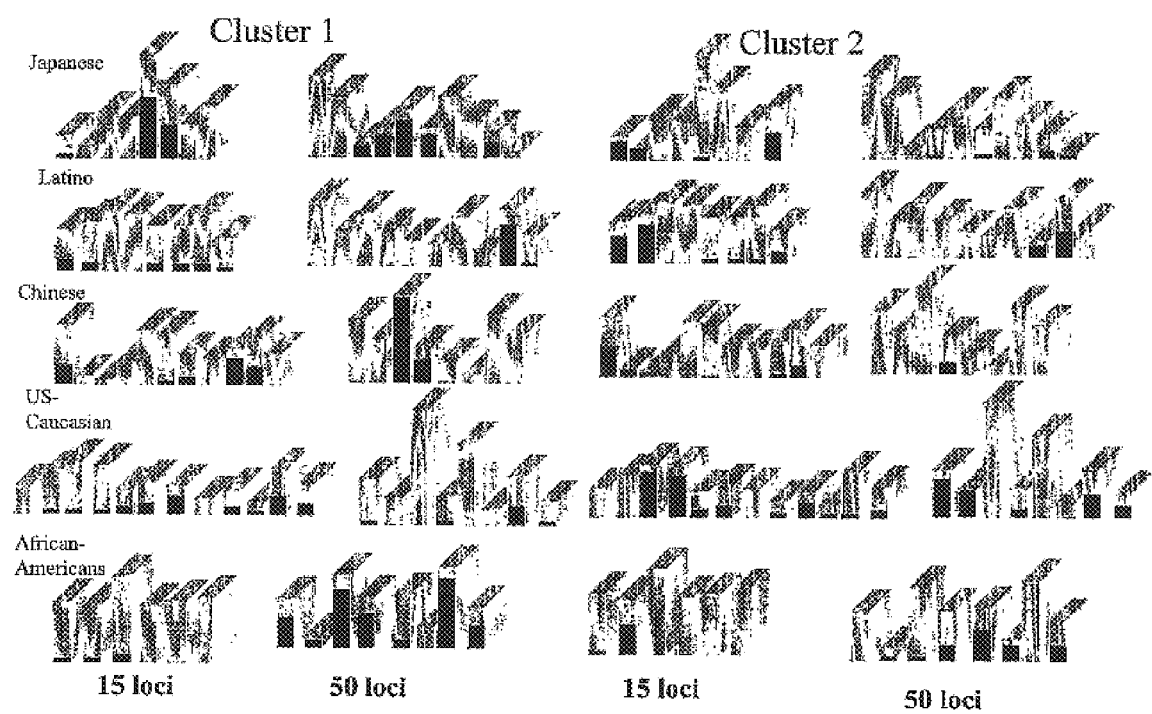
FIGS. 10, 11 & 12 show the identification of particular clusters, obtained from analyzing each ethnic group separately, by ethnic subpopulations from clusters obtained by analyzing all the ethnic groups as a total population. The shaded bars represent the separation into clusters of each ethnic group run separately with 15 or 50 loci (same data as that present in FIG. 9). The black bars represent the location of the individuals separated into clusters when the total population was analyzed with 15 or 50 loci (data present in FIGS. 2–7).
Figure 11:
Figure 12:
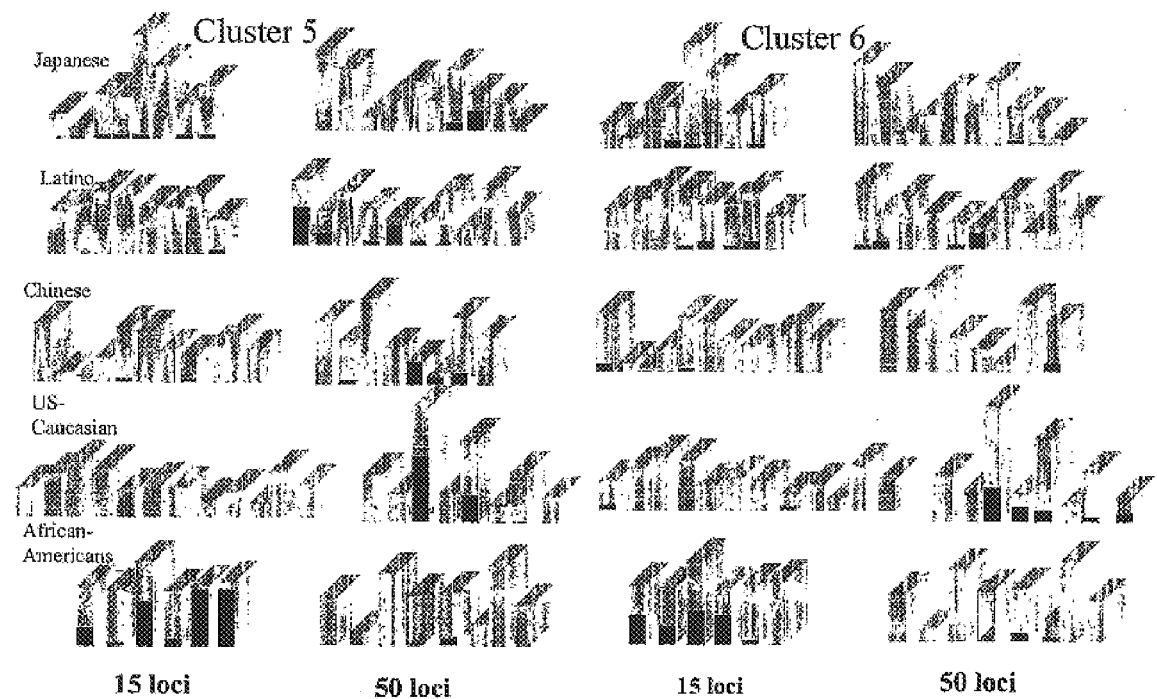

In addition, the ethnic groups identified in each cluster, when the analysis was done on the total population with 15 and 50 loci, do not fall into discrete clusters that result from the analysis with 15 or 50 loci for each ethnic group (FIGS. 10–12). The question addressed by this analysis, is whether the individuals of the ethnic groups that comprise a part of each cluster identified when the total population was analyzed, identify single clusters from the clusters that resulted when the ethnic group was individually analyzed. In fact, the individuals from the different clusters resulting from the total population analysis fall in more than one cluster resulting from the ethnic group analysis.

Thus, the ethnic groups themselves are genetically diverse and the subgroups identified by the total population analysis do not fall into the same genetic subgroups. This is true even for the African American subgroup using 15 loci from Cluster 5 and Cluster 6 (FIG. 12). These African American individuals that are the predominant group in these two clusters from the total population analysis, are found in almost all the clusters resulting from the clustering analysis of African Americans separately.

Example 2

Use of the Genetic Clustering Algorithm to Assess the Heterogeneity of the Populations in a CNS Case Study A study was designed to identify genes that predisposed to the development of a CNS disease. Candidate genes were selected because of their putative roles in the biology of the CNS disease. Five single nucleotide polymorphic (SNP) markers were developed from genomic regions containing these candidate genes and genotyped in both patient and control populations using the methods described in Example 1.

The patient population consisted of 140 predominantly Caucasian patients diagnosed with a CNS disease. Two populations were used as control groups. The first were 94 ethnically matched individuals who were ascertained to be free of psychiatric disease by history and psychiatric examination. The second group consisted of 95 ethnically matched individuals from the San Diego area who were reportedly healthy on the basis of history alone.

The genotypes were analyzed for differences in frequency between cases and controls as well as for allele frequency differences. Haplotype frequencies, based on combinations of SNP markers, were estimated in the case and control groups using expectation maximization algorithms and the significance of frequency differences was assessed by permutation analysis. This analysis indicated a significant frequency difference for one haplotype between the case population and the psychiatric disease-free control population. However, a similar analysis between the case population and the San Diego control revealed no significant difference. Therefore, the biological significance of this haplotype frequency difference was unclear.

Because this method of haplotype frequency estimation assumes population homogeneity, the cluster analysis tool of the invention was used to assess genetic diversity both in the combined population of case and control groups, as well as within the case and control groups separately.

Figure 13:
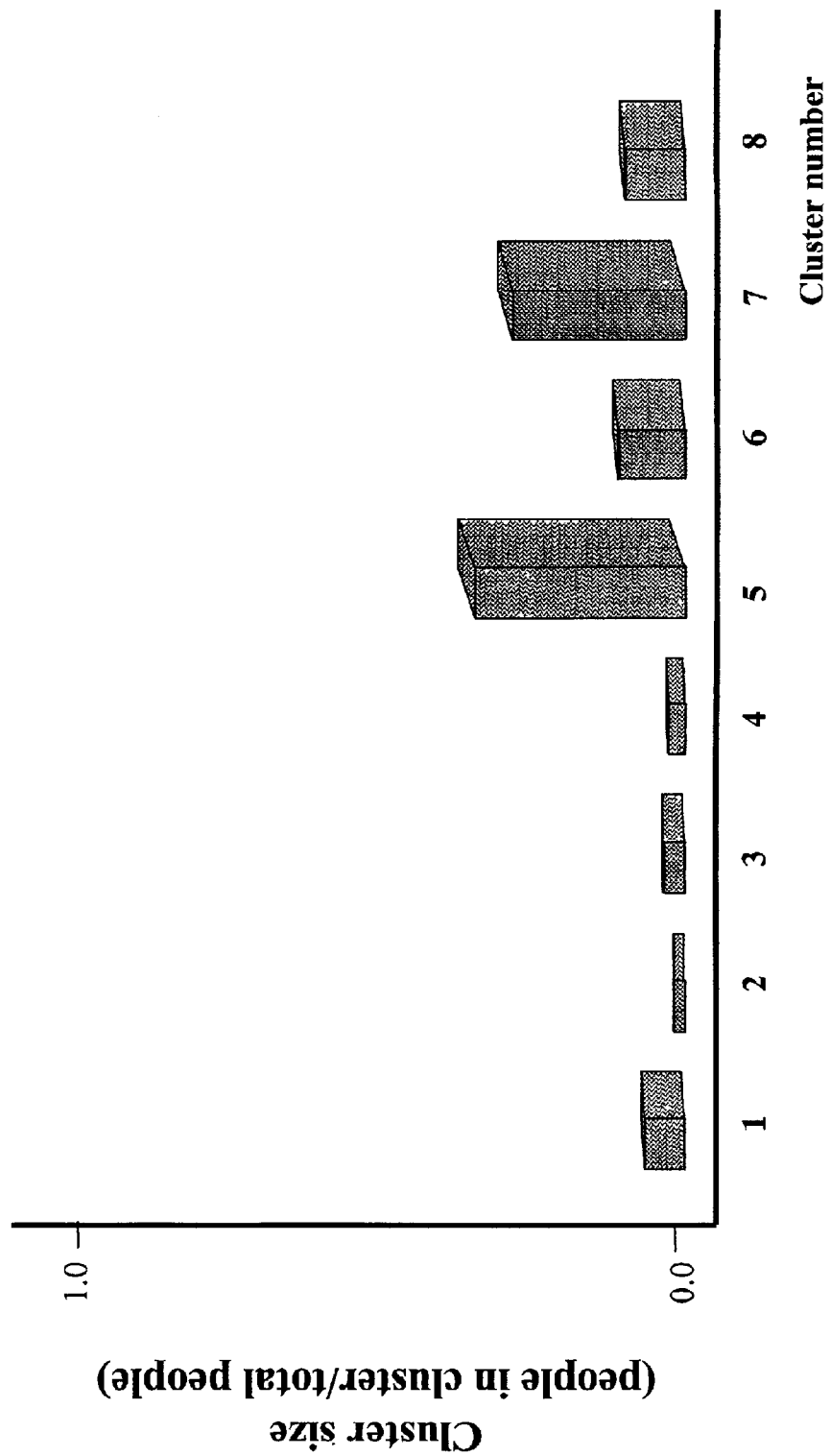
FIG. 13 shows a graphical representation of the results of the clustering analysis for the combined population (328 individuals: case and two controls).
Figure 14:
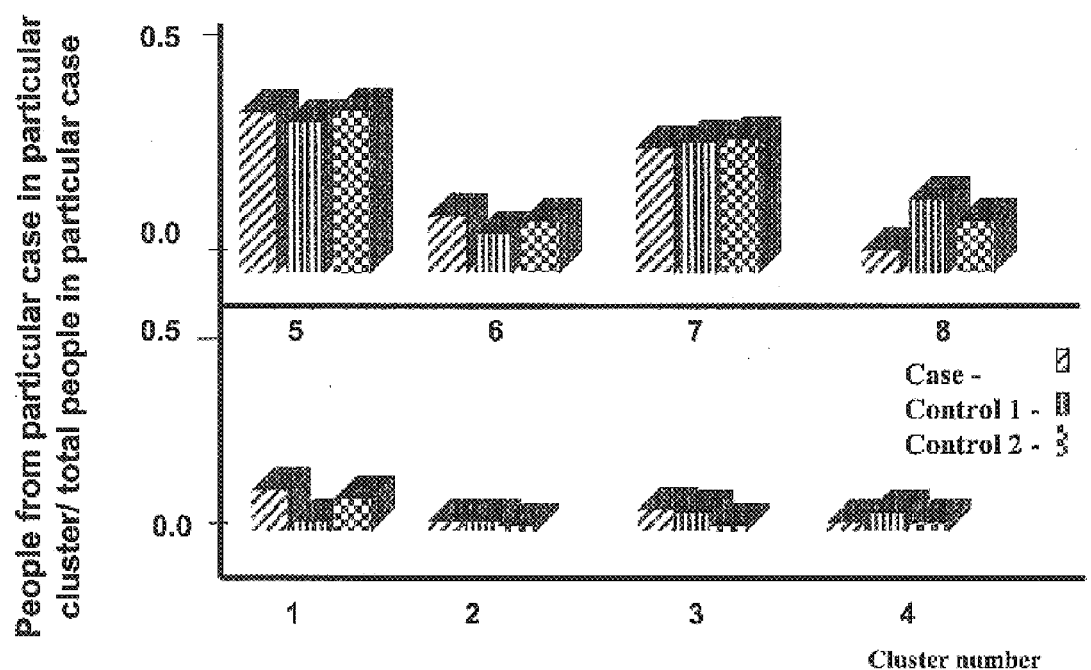
FIG. 14 shows a graphical representation of the proportion of individuals from case and control in each cluster.

When the combined population was analyzed for heterogeneity using the genetic clustering analysis of the invention (Detailed Description of the Invention) on the genotyping results from 5 loci, eight clusters were identified, not the two that would correspond to the case and control groups (FIG. 13). For each cluster, the proportion of case and control individuals was then determined (FIG. 14). Basically, all the clusters have approximately the same proportion of individuals from case and control except Cluster 1 and Cluster 8 (FIG. 14). Cluster 1 has a higher proportion of individuals from the case population, and a lower proportion of individuals from the matched control population, with the unmatched control population falling in the middle. In contrast, Cluster 8 has a higher proportion of matched control individuals, compared to case individuals, with the unmatched control group falling in the middle.

These data suggest that individuals in Clusters 2 through 7 are not genetically different for the loci studied, and that at least these loci are not linked to a potential genetic basis for the CNS disease. In contrast, the differences seen in Clusters 1 and 8 indicate that a subpopulation of individuals may be genetically distinct at these loci, and that these loci may be linked to a potential genetic basis for the CNS disease.

Figure 15:
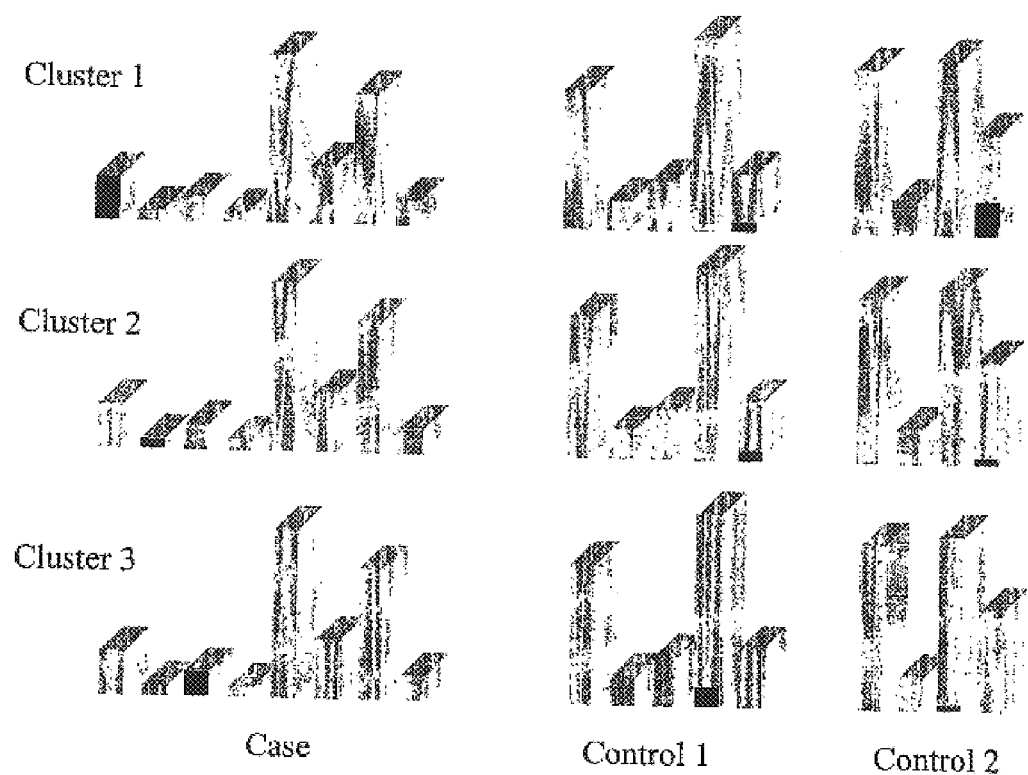
FIGS. 15, 16, and 17 show the identification of particular clusters, obtained from analyzing case and control populations separately, by case and control subpopulations from clusters identified by analyzing the case and control populations together.
Figure 16:
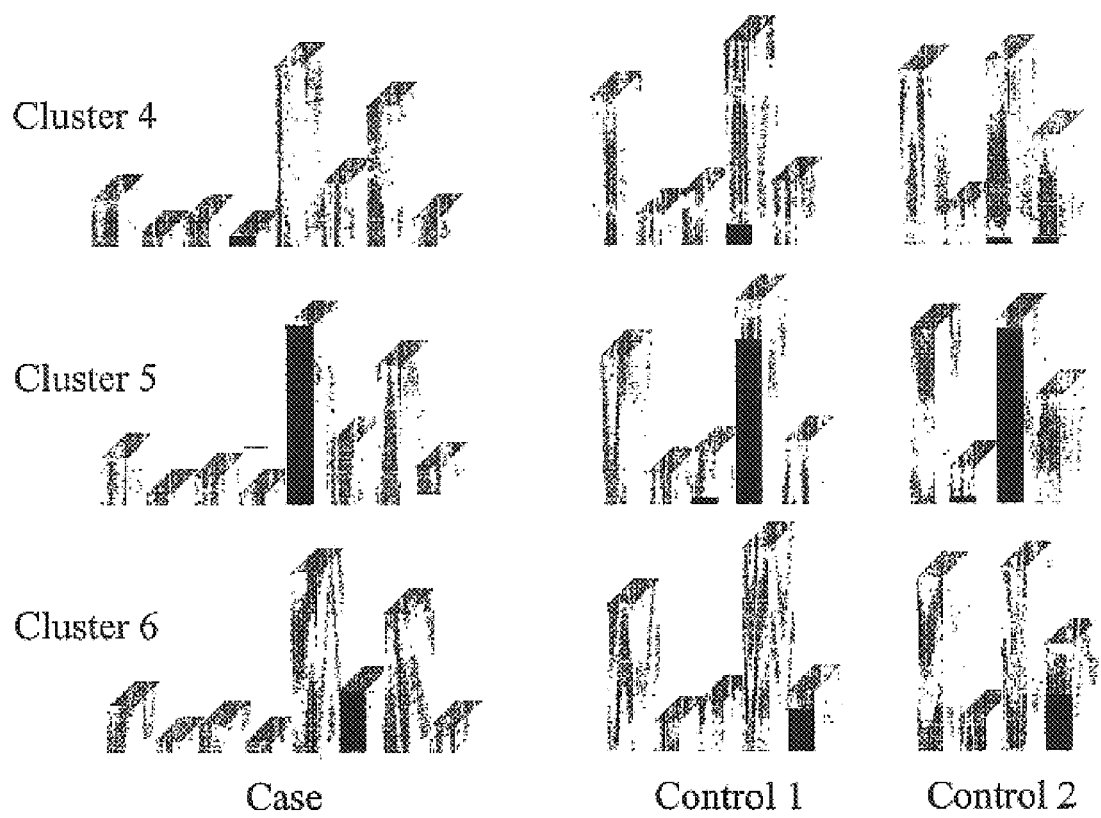
Figure 17:
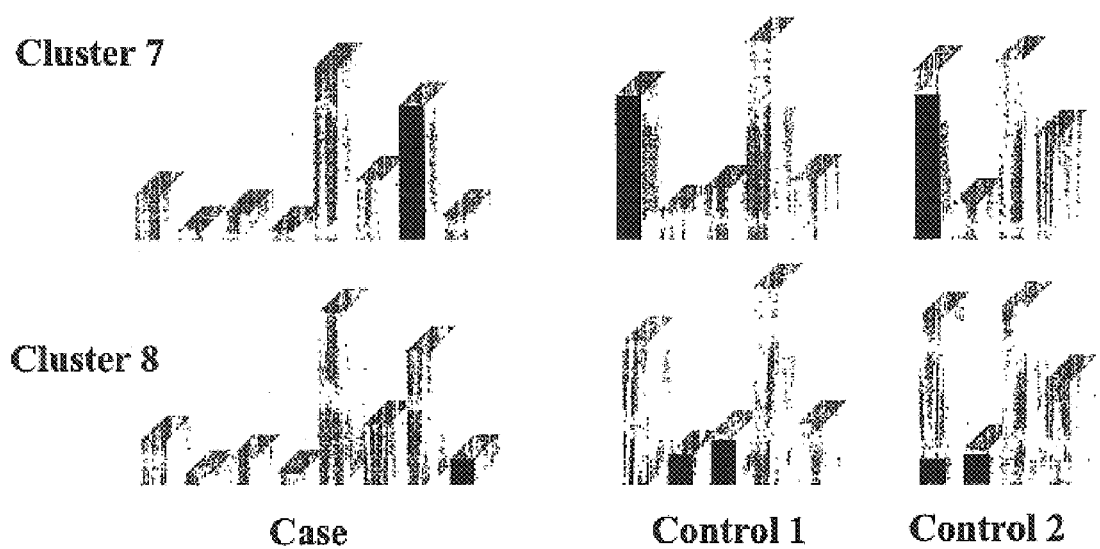

Subsequently, the homogeneity of the case and control groups individually was assessed using the genetic clustering analysis of the invention, and were found to be heterogenous (FIGS. 15–17). Then, the location of the case and control individuals separated into clusters in the total population was determined in the clusters from the analysis of the case and control populations separately (FIGS. 15-17). Interestingly, and in contrast to the ethnic diversity study (Example 2), the individual case and control clusters from the combined population generally identified single clusters generated from analyzing the case and control data separately.

What is claimed is:

1. A method of clustering members of a sample, comprising:
   a) applying a hierarchical clustering algorithm to said members of said sample;
   b) determining the optimal number of clusters based on the results of said hierarchical clustering algorithm; and
   c) distributing said members of said sample into said optimal number of clusters using non-hierarchical clustering.

2. The method of claim 1, further comprising:
   a) applying paired-pair analysis to said clusters in step c to determine whether said clusters should be further divided; and
   b) distributing said members into additional clusters based on the results of said paired-pair analysis.

3. The method of claim 1, further comprising constructing a similarity matrix prior to said applying step.

4. The method of claim 3, further comprising constructing a distance matrix from said similarity matrix prior to said applying step.

5. The method of claim 1, wherein said optimal number of clusters is found where the average pairwise intracluster similarity for two parent clusters is larger than the average pairwise intracluster similarity for a new cluster.

6. A computer system for determining clusters of members in a sample, comprising:
   a) First instructions for applying a hierarchical clustering algorithm to said members of said sample;
   b) Second instructions for determining the optimal number of clusters based on the results of said hierarchical clustering algorithm; and
   c) Third instructions for distributing said members of said sample into said optimal number of clusters using non-hierarchical clustering.

7. The computer system of claim 6, further comprising:
   a) Fourth instructions for applying paired-pair analysis to said clusters in step c to determine whether said clusters should be further divided; and
   b) Fifth instructions for distributing said members into additional clusters based on the results of said paired-pair analysis.

8. The computer system of claim 6, further comprising sixth instructions for constructing a similarity matrix prior to said applying step.

9. The computer system of claim 8, further comprising seventh instructions for constructing a distance matrix from said similarity matrix prior to said applying step.

10. The computer system of claim 6, wherein said optimal number of clusters is found where the average pairwise intracluster similarity for two parent clusters is larger than the average pairwise intracluster similarity for a new cluster.

11. A computer system for clustering members of a sample, comprising:
   a. First instructions for applying a non-hierarchical clustering algorithm to said sample;
   b. Second instructions for applying paired-pair analysis to pairs of homozygous pairs in any clusters resulting from said non-hierarchical clustering algorithm to determine whether said non-hierarchical clusters should be further divided; and
   c. Third instructions for distribution of said members into additional clusters based on the results of said paired-pair analysis.

12. A programmed storage device comprising instructions that when executed perform a method for clustering members of a sample, comprising:
   a) applying a hierarchical clustering algorithm to said members of said sample;
   b) determining the optimal number of clusters based on the results of said hierarchical clustering algorithm; and
   c) distributing said members of said sample into said optimal number of clusters using non-hierarchical clustering.

13. The programmed storage device of claim 12, further comprising:
   a) applying paired-pair analysis to said clusters in step c to determine whether said clusters should be further divided; and
   b) distributing said members into additional clusters based on the results of said paired-pair analysis.

14. The programmed storage device of claim 12, further comprising constructing a similarity matrix prior to said applying step.

15. The programmed storage device of claim 14, further comprising constructing a distance matrix from said similarity matrix prior to said applying step.

16. The programmed storage device of claim 12, wherein said optimal number of clusters is found where the average pairwise intracluster similarity for two parent clusters is larger than the average pairwise intracluster similarity for a new cluster.

\* \* \* \* \*

UNITED STATES PATENT AND TRADEMARK OFFICE
CERTIFICATE OF CORRECTION

PATENT NO. : 6,934,636 B1
DATED : August 23, 2005
INVENTOR(S) : Boguslaw A. Skierczynski and Nicholas J. Schork It is certified that error appears in the above-identified patent and that said Letters Patent is hereby corrected as shown below:

Column 2,
Line 23, "(Jin & Chalraborty," should read -- (Jin & Chakraborty, --.

Column 3,
Line 33, "said sun" should read -- said sum --.

Column 6,
Line 9, "the homozygousm" should read -- the homozygous --.

Column 9,
Line 40, "refers the identity" should read -- refers to the identity --.

Column 15,

Line 58, "$\overline{W}_{kl} \geq \overline{Z}$" should read -- $W_{kl} \geq \overline{Z}$ --.

Column 16,
Line 41, "or heterozygous in said" should read -- or heterozygotes in said --.

Column 17,
Line 5, "encompass anything" should read -- encompasses anything --.

Column 21,
Line 4, "to calculated millions," should read -- to calculate millions, --.

Signed and Sealed this

Seventh Day of February, 2006

JON W. DUDAS
*Director of the United States Patent and Trademark Office*